United States Patent
Ghahary et al.

(10) Patent No.: US 9,791,458 B2
(45) Date of Patent: Oct. 17, 2017

(54) DISSOLVED PROTEIN ARTHRITIS MARKERS

(75) Inventors: Aziz Ghahary, Vancouver (CA); Wolodymyr Walter Peter Maksymowych, Edmonton (CA); Ruhangiz Taghi Kilani, Vancouver (CA)

(73) Assignee: UNIVERSITY OF BRITISH COLUMBIA, Vancouver, British Columbia (CA)

( * ) Notice: Subject to any disclaimer, the term of this patent is extended or adjusted under 35 U.S.C. 154(b) by 89 days.

(21) Appl. No.: 12/637,730

(22) Filed: Dec. 14, 2009

(65) Prior Publication Data
US 2012/0003665 A1   Jan. 5, 2012

Related U.S. Application Data

(63) Continuation of application No. 12/300,118, filed as application No. PCT/CA2007/000817 on May 9, 2007, now abandoned.

(60) Provisional application No. 60/798,712, filed on May 9, 2006.

(51) Int. Cl.
*A61K 49/00* (2006.01)
*A61K 38/00* (2006.01)
*G01N 33/53* (2006.01)
*G01N 33/68* (2006.01)

(52) U.S. Cl.
CPC ... *G01N 33/6893* (2013.01); *G01N 2800/102* (2013.01)

(58) Field of Classification Search
None
See application file for complete search history.

(56) References Cited

U.S. PATENT DOCUMENTS

| | | | |
|---|---|---|---|
| 5,998,149 A * | 12/1999 | Hsich et al. | 435/7.1 |
| 7,171,311 B2 * | 1/2007 | Dai et al. | 702/19 |
| 7,396,654 B2 * | 7/2008 | Hayes et al. | 435/7.92 |
| 7,919,262 B2 * | 4/2011 | Yacoubian et al. | 435/7.1 |
| 7,939,272 B2 * | 5/2011 | Buck | 435/7.1 |
| 2005/0009094 A1 | 1/2005 | Mueller et al. | |
| 2005/0042681 A1 * | 2/2005 | Van Eyk et al. | 435/7.1 |
| 2008/0220013 A1 * | 9/2008 | Hochstrasser et al. | 424/198.1 |
| 2009/0093005 A1 * | 4/2009 | Smalley et al. | 435/7.92 |
| 2010/0016173 A1 * | 1/2010 | Nagalla et al. | 506/9 |
| 2011/0052573 A1 * | 3/2011 | Marrotta | 424/133.1 |
| 2012/0077695 A1 * | 3/2012 | Ostroff et al. | 506/9 |
| 2012/0101002 A1 * | 4/2012 | Riel-Mehan et al. | 506/9 |
| 2014/0121127 A1 * | 5/2014 | Speicher et al. | 506/9 |

FOREIGN PATENT DOCUMENTS

| EP | 07719741 | 5/2009 |
|---|---|---|
| WO | WO 97/33601 | 9/1997 |
| WO | WO 97/38315 | 10/1997 |
| WO | WO 98/26293 | 6/1998 |
| WO | WO 99/46401 | 9/1999 |
| WO | PCT/EP99/01545 | 11/1999 |

OTHER PUBLICATIONS

Van Everbroeck et al. 2005. J. Neurol Neurosurg Psychiatry. 76:100-102.*
Kilani et al. 2007. J. Rheumatol. 34:1650-1657.*
Leite J. Invitrogen Protein Analysis, www.invitrogen.com/piq. downloaded Jan. 4, 2013.*
14-3-3 eta antibodies, Santa Cruz Biotech, downloaded, Mar. 31, 2015.*
Furst et al 2005. Ann. Rheum Dis. 64:iv2-iv14.*
Scheiman et al. 2005. Arth. Res and Therap. 7(suppl 4):S23-S29.*
Da Siva et al. 2005. Ann. Rheum Dis. 2006. 65:285-293.*
https://www.scbt.com/scbt/product/14-3-3-eta-antibody-6a12, downloaded Apr. 17, 2017.*
Ubl et al. 2002 Molecular Brain Research 108:33-39.*
Ahrens, D. et al (1996) "Expression of Matrix Metalloproteinase 9 (96-kd Gelatinase B) in Human Rheumatoid Arthritis", Arthritis & Rheumatism, 39-9:1576-1587.
Ausubel, F., et al (1999) "Short Protocols in Molecular Biology", Ch. 11 Immunology, pp. 11-4-11-5, John Wiley & Sons, New York.
Ausubel, F., et al (2008) "Current Protocols in Molecular Biology", Ch. 1 Immunoassays, pp. 11.0.1-11.3.6, John Wiley & Sons, New York.
Bombara, M., et al (1993) "Cell Contact Between T Cells and Synovial Fibroblasts Causes Induction of Adhesion Molecules Arid Cytokines", J. Leukocyte Biology, 54:399-406.
Boston,P.,et al(1982)"Human 14-3-3 Protein:Radioimmunoassay,Tissue Distribution, and Cerebrospinal Fluid Levels in Patients With Neurological Disorders",J. N.Chem 38:1475-82.
Burger,D., et al(1998)"Imbalance Between Interstitial Collagenase and Tissue Inhibitor . . . ", Arthritis & Rheumatism, 41-10:1748-1759.
Chan, T., et al(1999) "14-3-3σ is Required to Prevent Mitotic Catastrophe After DNA Damage", Nature, 401:616-620.
Cho, M., et al (2004) "Effector Function of Type II Collagen-Stemulated T Cells FromRheumatoid Arthritis Patients", Arthritis & Rheumatism, 50-3:776-784.
Craparo,A.,et al (1997)"14-3-3(e) Interacts With the Insulin-Like Growth Factor I Receptor and Insulin Receptor Substrate . . . ", J. Biol. Chem. 272:116633-1166.
Du, X., et al(1994)"Association of a Phospholipase A2(14-3-3 Protein) With the Platelet Glycoprotein Ib-IX Complex", J. Biol. Chem. 269:18287-18290.
Firestein, G. S., (1997) "Rheumatoid Synovitis and Pannus", Rheumatology, pp. 5/13.1-5/13.5, Mosby, London.
Fu, H., et al ((2000)"14-3-3 Proteins: Structure, Function and Regulation", Annu. Rev. Pharmacol. Toxicol, 40:617-47.
Ghaffari, A., et al (2006) "Fibroblast Extracellular Matrix Gene Expression in Response to Keratinocyte-Releasable Stratifin", J. Cell Biochem. 98:383-393.
Ghahary, A., et al (2004) "Keratinocyte-Releasable Stratifin Functions as a Potent Collagenase-Stimulating Factor in Fibroblasts", J. Invest. Dermatol. 122:1188-1197.

(Continued)

*Primary Examiner* — Shulamith H Shafer
(74) *Attorney, Agent, or Firm* — Todd A. Lorenz

(57) ABSTRACT

Methods and kits for diagnosing arthritis are provided. The methods may involve detection of 14-3-3 eta or gamma proteins in a sera or synovial fluid sample.

9 Claims, 7 Drawing Sheets

(56) References Cited

OTHER PUBLICATIONS

Gilbert M. R., (2004) "Neurological Complications" in Abeloff MD, et al., Clinical Oncology, 3rd Ed., pp. 1213-1246, Churchill Livingstone/Elsevier Press, New York.

Harlow, E., and Lane, D., (1988) Antibodies: A Laboratory Manual, pp. 553-612, Cold Spring Harbor Laboratory Press, Cold Spring Harbor.

Hermeking, H., et al., (1997) "14-3-3σ is a p53-Regulated Inhibitor of G2/M Progression", Mol Cell, 1:3-11.

Hsich, G., et al. (1996)"The 14-3-3 Brain Protein in Cerebrospinal Fluid as a Marker for Transmissible Spongiform Encephalopathies", N Engl J. Med. 335:924-930.

Ichimura, T., et al., (1987)"Brain 14-3-3 Protein is an Activator Protein That Activates Tryptophan 5-Monooxygenase and Tyrosine . . . ", FEBS Lett. 04877, 219:79-82.

Ichimura, T., et al., (1988)Molecular Cloning of cDNA Coding for Brain-SPecific 14-3-3 Protein, A Protein Kinase-Dependent Activator . . . Proc. Natl Acad. Sci. 85:7084-7088.

Jamal, O. S., et al (1998) "Increased Expression of Human Type IIa Secretory Phospholipase A2 Antigen in Arthritic Synovium", Ann. Rheum Dis. 57:550-558.

Jasser, M. Z., et al., (1994) "Induction of Stromelysin-1 and Collagenase Synthesis in Fibrochondrocytes by Tumor Necrosis Factor-α", Matrix Biology 14:241-249.

Katrib, A., et al., (2002) "What Can We Learn From the Synovium in Early Rheumatoid Arthritis"., Inflamm. Res. 51:170-175.

Katz, A. B., et al., (1999)"A Partial Catalog of Proteins Secreted by Epidermal Keratinocytes in Culture". J. Invest Dermatol 112:818-821.

Kilani, R. T., et al.,(2007)"Detection of High Levels of 2 Specific Isoforms of 14-3-3 Proteins in Synovial Fluid From Patients With Joint Inflammation",J. Rheu. 34:1650-7.

Kim, Y. S., et al., (2005) "Role of 14-3-3η as a Positive Regulator of the Glucocorticoid Receptor Transcriptional Activation", Endocrinology 146:3133-3140.

Konttinen, Y. T., et al., (1998) "New Collagenolytic Enzymes/ Cascade Identified at the Pannus-Hard Tissue Junction in Rheumatoid Arthritis . . . ", Marix Biology 17:585-601.

Konttinen, Y. T., et al.,(1999) "Analysis of 16 Different Matrix Metalloproteinases (MMP-1 to MMP-20) in the Synovial Membrane . . . ", Ann. Rheum. Dis. 58:691-697.

Kresky, A. M., et al., (2001)"Immunomodulators: Immunosuppressive Agents, Tolerogens, and Immunostimulants", in Hardman— 10th Ed. pp. 1461-1483, McGraw Hill, New York.

Laronga, C., et al., (2000) Association of the Cyclin-Dependent Kinases and 14-3-3 Sigma Negatively Regulates Cell Cycle Progression:, J. Biol. Chem 275-30:2:3106-23112.

Lindy, O., et al., (1997) "Matrix Metalloproteinase 13 (Collagenase 3) In Human Rheumatoid Synovium", Arthritis & Rheumatism, 40-8:1391-1399.

Lipsky, P. E., et al., (2001) "Rheumatoid Arthritis", in Braunwald— Harrison's Principles of Internal Medicine, 15th Ed., pp. 1928-1937, McGraw Hill, New York.

Martin, H., et al., (1993) "Antibodies Against the Major Brain Isoforms of 14-3-3 Protein an Antibody Specific for the N-Acetylataed . . . ", FEBS 13058—331-3:296-303.

McInnes, I. B., et al., (2000) "Cell-Cell Interactoins in Synovitis Interactions Between T Lymphocytes and Synovial Cells", Arthritis Res. 2:374-378.

Miranda-Carus, M., et al., (2004) IL-15 and the Initiation of Cell Contact-Dependent Synovial Fibroblast-T Lymphocyte Cross-Talk . . . J. Immnol. 173:1463-1476.

Moore, B. W., et al., (1967) "Specific Acidic Proteins of the Nervous System", in Carson FD, pp. 343-359.

Neeck, G., et a., (2005) "Involvement of the Glucocorticoid Receptor in the Pathogenesis of Rheumatoid Arthritis", Ann. N.Y. Acad. Sci 966:491-495.

Pap, T., et al., (2000) "Differential Expression Pattern of Membrane-Type Matrix Metalloproteinases in Rheumatoid Arthritis", Arthritis Rheum, 43:1226-1232.

Poole, A. R. (2001) Cartilage in Health and Disease, in Koopman WJ—Arthritis and Allied Conditions, 14th Ed. pp. 226-284, Williams & Wilkins, Baltimore.

Sambrook, J., (2001) Molecular Cloning—Protein Interaction Technologies—A Laboratory Manual, pp. 655-688, Cold Spring Harbor Laboratory Press.

Smeets, TJM., et al., (2000) "The Effects of Interferon-B Treatment of Synovial Inflammation and Expression of Metalloproteinases . . . ", Arthritis & Rheumatism 43-2:270-274.

Sorsa, T., et al., (1992) "Collagenase in Synovitis of Rheumatoid Arthritis", Seminars in Arthritis and Rheumatism, 22-1:44-53.

Takahashi, S., et al., (2000) "Functional Interaction of the Immunosuppressant Mizoribine With the 14-3-3 Protein", Biochemical & Biophysical Res. Comm. 274:87-92.

Tohyama, C. T., et al., "Localization of Human Glucocortoid Receptor in Rheumatoid Synovial Tissue of the Knee Joint", Scand. J. Rheumatology, 22:44-53.

Toker, A., et al., (1990) "Protein Kinase C Inhibitor Proteins . . . ", Eur. J. Biochem. 191:421-429.

Tolboom, TCA., et al., (2002) "Invasive Properties of Fibroblast-like Synoviocytes: Correlation With Growth Characteristics . . . ", Ann. Rheum, Dis. 61:975-980.

Skogh, T., et al., (2003) "Twenty Eight Joint Count Disease Activity Score in Recent Onset Rheumatoid Arthritis Using C Reactive Protein . . . " Ann. Rheum Dis. 62:681-682.

Wilker, E., et al., (2004) "14-3-3 Proteins—A Focus on Cancer and Human Disease", J. Mol. Cell. 37:633-642.

Yaffe, M.B., et al., (2002) "How Do 14-3-3 Proteins Work?", FEBS Letters 513:53-57.

Yamamura, Y., et al., (2001) "Effector Function of Resting T Cells: Activation of Synovial Fibroblasts", J. Immunol. 166:2270-2275.

Xiao, et al (2005) "An Approach to Studying Lung Cancer-Related Proteins in Human Blood", Molecular & Cellular Proteomics 4:1480-1486, 2005.

Wakabayashi et al., "Increased concentrations of 14-3-3ε, γ and ζ isoforms in cerebrospinal fluid of AIDS patients with neuronal destruction," Clinica Chimica Acta, 312(1-2): pp. 97-105 (2001).

Ahrens D, Koch A E, Pope R M. Arthritis Rheum. 39:1576-1587, 1996.

Bombara M P, Webb D L, Conrad P. J. Leukocyte Biol. 54: 399-406, 1993.

Boston P F, Jackson P, Thompson R J. J. Neurochem. 38, 1475-82, 1982.

Burger D, Rezzonico R, Li J M, Modoux C, Pierce R A, Welgus H G, Dayer J M. Arthritis Rheum. 41(10):1748-59, 1998.

Chan T A, Hermeking H, Lengauer C, Kinzler K W, Volgelstein B. Nature 401:616-620, 1999.

Cho M L, Yoon C H, Hwang C Y. Arthritis Rheum. 50:776-784, 2004.

Craparo A, Freund R, Gustafson T (1997). J Biol Chem 272:11663-69.

F U H, Subramanian R R, Masters S C: Annu Rev Pharmacol Toxicol 40:617-647, 2000.

Firestein G S. (1997). Rheumatoid synovitis and pannus. In: J. H. Klippel and P. A. Dieppe, Editors, Rheumatology, Mosby, London, pp. 5/13.1-5/13.5, 1997.

Ghaffari A, Li Y, Karami A, Ghaffari M, Tredget E E, Ghahary A. J. Cell. Biochem. Jan. 2006.

Ghahary A, Karimi-Busheri F, Marcoux Y, Li Y, Tredget E E, Kilani R T, Li L, Zheng J, Karami A, Keller B, Weinfeld M. J. Invest. Dermatol. 122(5): 1188-1197, 2004.

Harris E D Jr., Cytokines, Lymphokines, Growth Factors, and Chemokines. In: Rheumatoid Arthritis. Philadelphia: W.B. Saunders Company, 1997: 105-125.

Harris E D Jr., History and Epidemiology of Rheumatoid Arthritis: How long has it affected us, and who is at risk? In: Rheumatoid Arthritis. Philadelphia: W.B. Saunders Company, 1997: 21-27.

Harris E D Jr., Introduction. In: Rheumatoid Arthritis. Philadelphia: W.B. Saunders Company, 1997: xix-xxiii.

(56) References Cited

OTHER PUBLICATIONS

Harris E D Jr., Rheumatoid Synovium: Complex, and More Than the Sum of its Parts. In: Rheumatoid Arthritis. Philadelphia: W.B. Saunders Company, 1997: 126-149.

Hermeking H, Lengauer C, Polyak K, He T C, Zhang L, Thiagalingam S, Kinzler K W, Volgelstein B. Mol Cell 1:3-11, 1997.

Hsich G, Kenney K, Gibbs C J, Lee K H, Harrington M G: N Engl J Med 335:924-30, 1996.

Ichimura T, Isobe T, Okuyama T, Yamauchi T, Fujisawa H (1987) FEBS Lett. 219:79-82.

Ichimura T, Isobe T, Okuyama T, Takahashi N, Araki K, Kuwano R, Akahashi Y (1988). Proc Natl Acad Sci USA, 85:7084-8.

Jasser, M. Z., Mitchell P. G. and Cheung, H. S.: Induction of stomelysin-1 and collagenases synthesis in fibrochondrocytes by TNF-alpha. Matrix Biology 14: 241, 1994.

Katrib. A, McNeil H P, Youssef P P: Inflamm. Res. 51: 170-175, 2002.

Katz A B, Taichman, L B. J Invest Dermatol 112:818-821, 1999.

Konttinen Y T, Ceponis A, Takagi M, Ainola M, Sorsa T, Sutinen M, et al. Matrix Biol. 17:585-601, 1998.

Laronga C, Yang H Y, Neal C, Lee M H (2000). J. Biol. Chem. 275:23106-23112.

Lindy O, Konttinen Y T, Sorsa T. Arthritis Rheum. 40:1391-1399, 1997.

McInnes I B, Leung B P, Liew F Y. Arthritis Res. 2(5):374-8.34, 2000.

Miranda-Carus M E, Balsa A, Benito-Miguel M, Perez de Ayala C, Martin-Mola E. J. Immunol. 173:1463-1476, 2004.

Moore et al. 1967, in Carlson FD (ed) Physiol. and Biochem Aspects of Nervous INteg 343-359.

Pap T, Shigeyama Y, Kuchen S. (2000). Arthritis Rheum. 43: 1226-1232.

Poole A R; Cartilage in health and disease. In: Koopman W J. Ed. Arthritis and Allied conditions. A textbook of rheumatology. 14th ed. Baltimore: Williams and Wilikins, 2001: 226-284.

Smeets T J M, Dayer J M, Karan M C. Arthritis Rheum. 43:270-274, 2000.

Sorsa T, Konttinen Y T, Lindy O. Arthritis Rheum. 22: 44-53, 1992.

Toker A, Ellis C A, Sellers L A, Atiken A 1990. Eur J Biochem 191:421-429.

Tolboom T C A, Pieterman E, van der Laan W E. Ann. Rheum. Dis. 61: 975-980, 2002.

Wilker E, Yaffe M B: J Mol Cell Cardiol 37: 633-642, 2004.

Y. Yamamura, R. Gupta, Y. Morit, X. He, R. Pai, J. Endres, A. Freiberg, K. Chung and D. A. Fox. J. Immunol. 166 (2001), pp. 2270-2275.

Yaffe M B (2002). FEBS Lett 513(1):53-57.

* cited by examiner

DISSOLVED PROTEIN ARTHRITIS MARKERS

CROSS REFERENCES TO RELATED APPLICATIONS

This application claims priority under all applicable laws, to U.S. patent application Ser. No. 12/300,118, filed Nov. 6, 2008 now abandoned; International Application PCT/CA2007/000817 (WO 2007/128132), filed on May 9, 2007, designating the United States, which claims priority to United States Provisional patent application Ser. No. 60/798,712, filed May 9, 2006, each of which priority disclosures is incorporated herein by reference in its entirety.

SEQUENCE LISTING

The instant application contains a Sequence Listing which has been submitted in ASCII format via EFS-Web and is hereby incorporated by reference in its entirety. Said ASCII copy, created on Oct. 11, 2010, is named SMAR1202.txt and is 40,522 bytes in size.

FIELD OF THE INVENTION

The invention relates to assays for selected protein isoforms that are diagnostic biomarkers for arthritis when those proteins are found in extracellular fluids.

BACKGROUND OF THE INVENTION

Arthritis or arthralgia generally refers to inflammatory disorders of the joints of the body, and is usually accompanied by pain, swelling and stiffness. Arthritis may result from any of several causes including infection, trauma, degenerative disorders, metabolic disorders or disturbances or other unknown etiologies. Arthritis may be more specifically described as, for example, rheumatoid arthritis, osteoarthritis, bacterial or infectious arthritis. Arthritis may further accompany other identified disorders, including gout, ankylosing spondylitis, inflammatory bowel disease or psoriasis.

In normal joints, a small amount of synovial fluid (SF) lubricates cartilage and the synovium, and acts as a reservoir for solutes and a few resting mononuclear and synovial cells (3). During chronic inflammation, SF volume and the concentration of immune cells and soluble proteins increase (4).

For some forms of arthritis, such as rheumatoid arthritis (RA), the specific cause may not be known. RA is regarded as a "multifactorial threshold model", in which many genetic and environmental influences must act on the same person in order for the disease to manifest (1). As a specific target is lacking, current therapies are primarily aimed at suppression of the inflammatory response (2). A hallmark of RA is synovial hyperplasia, characterized by fibroblast-like synoviocyte (FLS) proliferation and inflammatory cell infiltration into the subintima, or outer layer of the synovium (5). The FLS, which comprise about two-thirds of the synovium population, have a well-defined secretory system (5) and secrete large amounts of destructive matrix metalloproteases (MMPs) in RA (6), specifically MMP-1, 3, 8, 9, 10, 11 and 13 (7-11). Numerous researchers have shown that MMP-1 and MMP-3 play important roles in RA (12) and that the collagenase (MMP-1) is the most abundant (6). Both MMP-1 and MMP-3 are biomarkers that have been shown to have predictive validity for structural damage in RA. Local expression of MMPs in arthritis, especially MMP-1, is particularly prominent in the joint pannus adjacent to the site of cartilage and bone destruction (13). The collagenases, particularly MMP-1, cleave native collagen molecules at neutral pH, rendering the collagen susceptible to further enzymatic degradation (14).

Known factors that activate FLS to produce MMP-1 include pro-inflammatory cytokines such as interleukin-1 (IL-1) and tumour necrosis factor alpha (TNF-alpha), and both are involved in RA (15). IL-1alpha and TNF-alpha are capable of stimulating the production of other MMPs and stromelysins in synovial fibroblasts and chondrocytes in vitro (16). The interactions of FLS with TNF-alpha or IL-1 alpha from activated T cells induces expression of MMP-1 (17). T-cells can also activate FLS to produce an array of inflammatory mediators (18). This cyclical feedback loop between FLS and T cells and their respective cytokines lead to activation and proliferation of T cells and favours the persistent inflammation observed in RA (19-21). It has been suggested that therapeutic anti-TNF alpha antibodies neutralize TNF alpha and block the T cell activation that leads to this persistent state (22).

14-3-3 proteins are a family of dimeric proteins involved in a range of functions (23-24). There are seven mammalian 14-3-3 isoforms: beta ($\beta$), gamma ($\gamma$), epsilon ($\epsilon$), eta ($\eta$), sigma ($\sigma$), tau ($\tau$) and zeta ($\zeta$). Since the discovery of the first 14-3-3 protein in 1967 (26), the members of the 14-3-3 protein family have been repeatedly re-discovered based on their new biological activities, primarily in signal transduction pathways. They have been identified as activators of tryptophan and tyrosine hydroxylase (27-28) and PKC inhibitors (29). Subsequent studies identified the 14-3-3 proteins as molecules that interact with PKCs, Raf family members and now more than 200 other intracellular proteins with critical biological functions (30-31) including cellular response to DNA damage and cell cycle regulation (32-34).

SUMMARY OF THE INVENTION

The invention is based in part on the surprising discovery that particular isoforms of the 14-3-3 protein, 14-3-3 eta and gamma, are present at increased levels in the serum and synovial fluid of arthritis patients, compared to normal patients.

In accordance with one aspect of the invention, there is provided a method for predicting responsiveness of a subject to a therapeutic regimen, the subject having, or suspected of having arthritis, the method comprising determining a presence, absence, amount or relative levels of a protein 14-3-3 eta or gamma in a sample, wherein the presence, absence, amount or relative level of the isoform is indicative of a sensitivity of the subject's arthritis to the therapeutic regimen.

In accordance with another aspect of the invention, there is provided a kit for detecting a 14-3-3 eta or gamma protein in a patient sample, such as a sample of sera or synovial fluid from a patient having, or at risk of having, an arthritis. The kit may comprise at least one antibody specific for detecting at least one of these isoforms of the 14-3-3 protein. The kit may further comprise at least one antibody specific for detecting at least one matrix metalloproteinase.

In accordance with another aspect of the invention, there is provided a method for selecting a group of subjects for determining the efficacy of a therapeutic regimen known or suspected of being useful for the treatment of arthritis, the method comprising detecting a presence, absence, amount or relative levels of a 14-3-3 eta or gamma protein in a patient sera or synovial fluid sample, wherein said presence, absence, amount or relative level of one or more of these isoforms of the 14-3-3 protein in that fluid is indicative of a sensitivity of the subject's arthritis to the therapeutic regimen.

In accordance with another aspect of the invention, there is provided a method of treating arthritis in a mammalian subject in need thereof, the method comprising administering to the subject a therapeutic regimen, wherein the presence, absence, amount or relative level of a 14-3-3 eta or gamma protein isoform in sera or synovial fluid from that subject is indicative of sensitivity to the therapeutic regimen.

In accordance with another aspect of the invention, there is provided a method of treating arthritis in a mammalian subject in need thereof, the method comprising: selecting a subject having a presence, absence, amount or relative level of 14-3-3 eta or gamma protein in sera or synovial fluid that is indicative of sensitivity to a therapeutic regimen; and administering to the subject the therapeutic regimen.

In accordance with another aspect of the invention, there is provided a method of identifying a mammalian subject with an increased sensitivity to a therapeutic regimen for treating arthritis, comprising the step of screening a population of subjects for the presence, absence, amount or relative level of 14-3-3 eta or gamma protein in sera or synovial fluid, and identifying subjects sensitive to the therapeutic regimen based at least in part on the presence, absence, amount or relative level of the protein in the fluid.

In selected embodiments, the invention may involve assays for other arthritis markers in the sera or synovial fluids of subjects, in conjunction with assays for the presence, absence, amount or relative level of 14-3-3 eta or gamma proteins. For example, assays of the invention may additionally involve determining the presence, absence, amount or relative levels of one or more matrix metalloproteinases, such as MMP-1 or MMP-3, in sera or synovial fluid samples.

BRIEF DESCRIPTION OF THE DRAWINGS

In drawings which illustrate embodiments of the invention.

Figure 1:
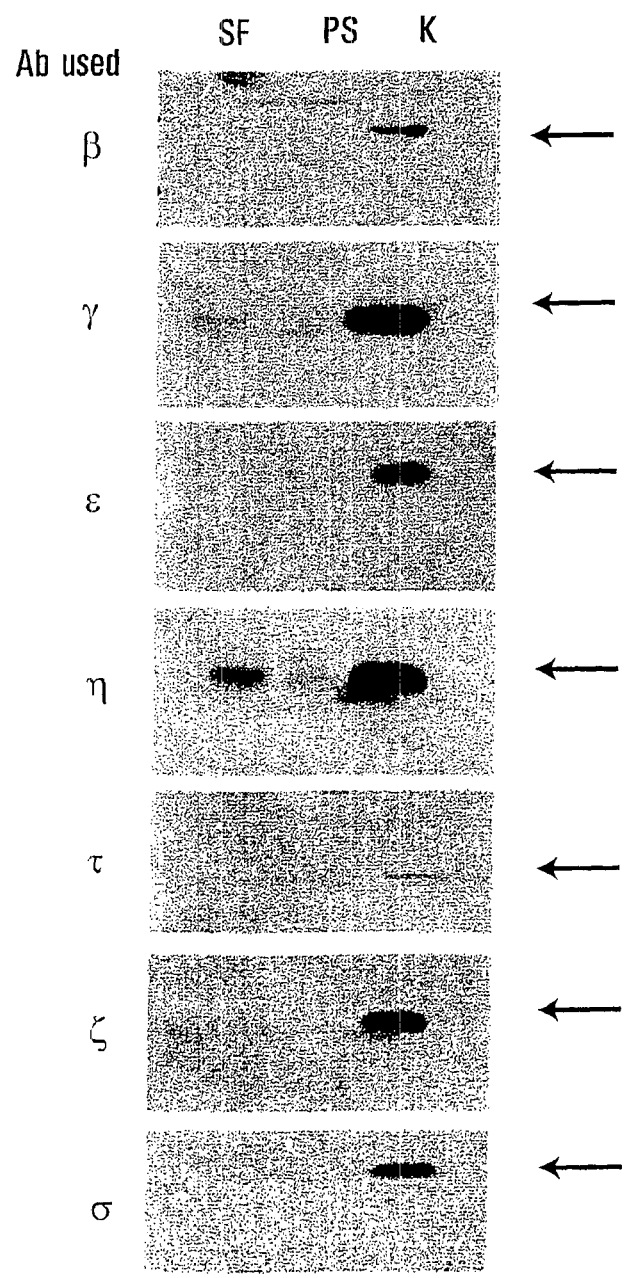
FIG. 1

Detection of various isoforms of 14-3-3 in the synovial fluid (SF) and serum (PS) of arthritic patients by western blot. Keratinocyte lysates (K) was used as a positive control.

FIG. 2.

Detection of 14-3-3 η in the synovial fluid of 17 arthritic patients. Synovial fluid samples (2 μl/lane) were taken from 17 RA patients who had active synovitis and analyzed by western blot, using an isoform-specific antibody for the 14-3-3 η isoform. Keratinocyte lysate (K) was used as a positive control. Levels of 14-3-3 η vary in the patient population surveyed, but is reliably detected in all synovial fluid samples.

FIG. 3

14-3-3 η, MMP-1 and MMP-3 expression in patient sera and synovial fluid. 12 patients' matched synovial fluid and serum samples examined by western blot. Keratinocyte cell lysate (K) was used as a positive control. SF: synovial fluid; PS: patient serum; MMP-1: matrix metalloproteinase 1; MMP-3: matrix metalloproteinase 3.

FIG. 4

Detection and comparison of the levels of 14-3-3 η and γ in 9 matched patient serum and synovial fluid samples. Patients' synovial fluid or serum (2 μl/lane) was analyzed by western blot using anti 14-3-3 η or γ antibody. Keratinocyte cell lysate (K) was used as a positive control. SF, synovial fluid; PS, patient serum.

FIG. 5

Levels of 14-3-3 η in matched patient serum and synovial fluid samples were quantified by densitometry and depicted in lower panel. Solid bars show the level of 14-3-3 η in serum normalized to a synovial fluid sample from the same patient (open bars).

FIG. 6

Detection of 14-3-3 η, γ, MMP-1 and MMP-3 in different volumes of normal and patients sera.

A) Pooled samples of 12 normal or patient sera were prepared and a range of volumes (0.1-2.0 μl/lane) were analyzed by western blot, using specific antibodies for 14-3-3 η, γ, MMP-1 or MMP-3. 2 μl of a pooled of synovial fluid (SF) from affected patients was included as a positive control. B) Recombinant 14-3-3 η isoform (0.01-2.0 μg/lane) was analyzed by western blot in parallel with 2 μl of normal (NS) or patient serum (PS).

FIG. 7

Illustrates detection of 14-3-3 η before and after anti-TNF therapy: Levels of 14-3-3 eta protein in 4 ml of serum samples from RA patients before (U) and after anti-TNF-a (T) Treatment. N=negative control which is 4 ml of a pooled serum sample prepared from 12 serum samples taken from 12 healthy individuals. P=positive control which is 4 mg of keratinocyte cell lysate total protein.

DETAILED DESCRIPTION

A "Disease Activity Score" (DAS) refers to a measure of the activity or state of rheumatoid arthritis in a patient. DAS is one of several standards or scores used in clinical practice. A calculation of a DAS may include the following parameters: Number of joints tender to the touch (TEN), number of swollen joints (SW), erythrocyte sedimentation rate (ESR) and patient assessment of disease activity (VAS). Alternatively, a DAS may include C-reactive protein marker assessment (CRP) (Skogh T et al 2003. Ann Rheum Dis 62:681-682).

A patient or test subject, as used herein, includes a human patient undergoing, or about to undergo, treatment for arthritis. A test subject includes non-human mammals undergoing, or about to undergo, treatment for arthritis. In the case of a test subject, the arthritis may be deliberately induced or implanted, or may develop spontaneously. The patient or test subject may have been previously diagnosed using methods described herein, for example, or other diagnostic methods known in the art, or may be selected as part of general population (a 'control' patient or 'control' test subject). Patients and test subjects, whether control or not, may be generally referred to as a subject. Patients may be selected or differentiated on the basis of disease severity, gender, age, or suitability for a particular treatment or assay method.

As used herein, an 'isoform' refers to any two or more of functionally similar proteins that have a similar but not identical amino acid sequence and are either encoded by different genes or by RNA transcripts from the same gene which have had different exons removed.

It will be appreciated by a person of skill in the art that the numerical designations of the positions of nucleotides or amino acids within a sequence are relative to the specific sequence. Also, the same positions may be assigned different numerical designations depending on the way in which the sequence is numbered and the sequence chosen. Furthermore, sequence variations such as insertions or deletions, may change the relative position and subsequently the numerical designations of particular nucleotides or amino acids at or around a particular site.

The terms 'peptide', 'polypeptide' and protein' may be used interchangeably, and refer to a compound comprised of at least two amino acid residues covalently linked by peptide bonds or modified peptide bonds, for example peptide isosteres (modified peptide bonds) that may provide additional desired properties to the peptide, such as increased half-life. A peptide may comprise at least two amino acids. The amino acids comprising a peptide or protein described herein may also be modified either by natural processes, such as posttranslational processing, or by chemical modification techniques which are well known in the art. Modifications can occur anywhere in a peptide, including the peptide backbone, the amino acid side-chains and the amino or carboxyl termini. It is understood that the same type of modification may be present in the same or varying degrees at several sites in a given peptide.

Nomenclature used to describe the peptide compounds of the present invention follows the conventional practice where the amino group is presented to the left and the carboxy group to the right of each amino acid residue. In the sequences representing selected specific embodiments of the present invention, the amino- and carboxy-terminal groups, although not specifically shown, will be understood to be in the form they would assume at physiologic pH values, unless otherwise specified. In the amino acid structure formulae, each residue may be generally represented by a one-letter or three-letter designation, corresponding to the trivial name of the amino acid.

The term 'antibody' as used herein includes polyclonal and monoclonal antibodies, chimeric, single chain, or humanized antibodies, as well as Fab or F(ab)$^2$ fragments, including the products of an Fab or other immunoglobulin expression library. Methods of making such antibodies or fragments are known in the art and may be found in, for example HARLOW, E and LANE D. Antibodies: A Laboratory Manual. 1988. Cold Spring Harbor Laboratory Press. Selection or identification of specific peptides for use as epitopes for production of antibodies that differentiate between proteins, or isoforms of proteins may be made using sequence comparisons—one of skill in the art will be able to identify suitable peptide or protein sequences that may be useful for producing antibodies with the desired selectivities. Examples of sequences that may be useful to one of skill may include SEQ ID NOs: 1-7.

As used herein, 'arthritis' or 'arthralgia' refer to an inflammatory disorder of the joints of the body. Pain, swelling, stiffness and difficulty of movement are frequently associated with arthritis diseases. Arthritis may result from any of several causes including infection, trauma, degenerative disorders, metabolic disorders or disturbances or other unknown etiologies. Arthritis may be more specifically described as, for example, rheumatoid arthritis, osteoarthritis, bacterial or infectious arthritis. Arthritis may further accompany other identified disorders, including gout, ankylosing spondylitis, inflammatory bowel disease or psoriasis. 14-3-3 proteins, particularly the eta and gamma isoforms, may be readily detected in synovial fluid or serum of patients affected with arthritis, for example rheumatoid arthritis. In one embodiment of the invention, detection of these signal transduction proteins in the site of inflammation may have application in early or more simplified diagnosis of arthritis, or differentiation between the various types of arthritis in a patient. Alternatively, the presence or relative levels of isoforms of 14-3-3 proteins may be a prognostic indicator of early-stage arthritis, before it progresses to a debilitating form. An advantage of early prognosis or diagnosis is earlier implementation of a treatment regimen. Alternatively, the presence or relative levels of isoforms of 14-3-3 in a patient sample may be useful to determine patient suitability for a particular treatment regimen.

Treatment regimens for various types of arthritis are known in the art. Therapeutic approaches to arthritis may for example be generally characterised as disease modifying therapy for arthritis, or remittive therapies. For example, a patient diagnosed with rheumatoid arthritis may be prescribed non-steroidal anti-inflammatory medications (NSAIDs) initially, to ease the discomfort and reduce the inflammation. Other treatment regimens may include, for example cyclooxygenase 2 specific inhibitors (CSIs), glucocorticoids, disease-modifying anti-rheumatic drugs (DMARDs), anti-TNF alpha neutralizing agents or immunosuppressive or cytotoxic drugs. Details on dosage or examples of particular drugs will be known to those of skill in the art, and may be found in, for example Harrison's Principles of Internal Medicine 15$^{th}$ ed. BRAUNWALD et at eds. McGraw-Hill or "The Pharmacological basis of therapeutics", 10$^{th}$ edition. HARDMAN H G., LIMBIRD L E. editors. McGraw-Hill, New York, and in "Clinical Oncology", 3$^{rd}$ edition. Churchill Livingstone/Elsevier Press, 2004. ABELOFF, M D. editor.

In another embodiment of the invention, the presence or relative levels of 14-3-3 eta or gamma proteins may correlate with the presence or relative levels of other proteins in the patient sample, for example matrix metalloproteinases (MMPs), such as MMP-1 or MMP-3. MMPs are zinc-binding endopeptidases that degrade components of the extracellular matrix. MMPs have different substrate specificities and are encoded by different genes. At least 25 different MMPs have been identified. Detection of 14-3-3 eta or gamma proteins in combination with at least one MMP in a patient sample may have application in early or more simplified diagnosis of arthritis, or differentiation between the various types of arthritis in a patient. Alternatively, the presence or relative levels of eta or gamma isoforms of 14-3-3 proteins in combination with at least one MMP in a patient sample may be a prognostic indicator of early-stage arthritis, before the arthritis progresses to a debilitating form. An advantage of early prognosis or diagnosis may include earlier implementation of a treatment regimen. Alternatively, the presence or relative levels of eta or gamma isoforms of 14-3-3 in combination with at least one MMP in a patient sample may be useful to determine patient suitability for a particular treatment regimen.

In another embodiment of the invention, a kit for detecting the presence of 14-3-3 eta or gamma proteins or particular MMPs in a patient sample, the kit being suitable for use in providing a diagnostic or prognostic result suitable for diagnosing or differentiating various types of arthritis. A kit may include, for example, antibodies specific for eta or gamma isoforms of 14-3-3 proteins. Such a kit may further include antibodies specific for particular MMPs. The kit may further include other reagents necessary for the detection of 14-3-3 eta or gamma or MMPs immunologically, such as labelled secondary antibodies, chromogenic or fluorogenic reagents, polymerization agents and/or instructions for using the kit for diagnostic or prognostic purposes.

General Methods

Once a subject is identified as being at risk for developing or having arthritis, information useful for assessing the disease state of the diagnosed arthritis, response to a therapeutic treatment regimen for arthritis, or prognosis of arthritis, or the type of arthritis may be obtained from the patient or test subject. Various methods for obtaining biological samples from a subject that contain protein or peptides that may be useful as biomarkers are known in the art. For example, tissue samples may be obtained by curettage, needle aspiration biopsy or needle (core) biopsy, incisional biopsy for sampling a tumor, or excisional biopsy, which may entail total removal of the tissue of interest. Alternatively, other bodily samples that contain genetic material, such as synovial fluid, hair, sputum, urine, stool, semen, plasma, serum or blood may be collected using methods known in the art.

The presence of specific proteins or peptides in a biological sample, or the relative levels of specific proteins or peptides in a biological sample may be detected by any of several methods known in the art. Examples of such methods include mass spectroscopy, immunological-based techniques such as western blotting, ELISA, immunohistochemistry, FACS, surface plasmon resonance or chromatography. Methods for these and other techniques may be found in, for example AUSUBEL et al., Current Protocols in Molecular Biology, John Wiley & Sons, New York, N.Y., 1998: ABELOFF, Clinical Oncology, $3^{rd}$ edition. Churchill Livingstone/Elsevier Press, 2004; HARLOW, E and LANE D. Antibodies: A Laboratory Manual. 1988. Cold Spring Harbor Laboratory Press; SAMBROOK J and RUSSELL D W. Molecular cloning: A Laboratory Manual 2001 Cold Spring Harbor Laboratory Press; Harrison's Principles of Internal Medicine $15^{th}$ ed. BRAUNWALD et al eds. McGraw-Hill. 14-3-3 detection methods are described for example in WO 99/46401, US 2005/9094, WO 97/38315 and WO 97/33601, all of which are incorporated herein be reference.

Western Blotting

Synovial fluid or serum (2 µl of each) was subjected to SDS-PAGE analysis with 12% (wt/vol) acrylamide gel, and electrotransferred onto PVDF membranes (Millipore Corporation). Non-specific proteins on membranes were blocked in 5% skim milk powder in PBS-0.1% Tween-20 overnight. Immunoblotting was performed using 2 µg/ml of 7 isoforms specific rabbit anti-human 14-3-3 polyclonal antibodies (Martin H, Patel Y, Jones D, Howell S, Robinson K and Aitken A 1993. *Antibodies against the major brain isoforms of 14-3-3 protein. An antibody specific for the N-acetylated amino-terminus of a protein. FEBS Letters.* 331:296-303). The membranes were then incubated with the appropriate secondary horseradish peroxidise conjugated anti-rabbit IgG (Sigma, St Louis, USA) or anti-mouse IgG (Bio-Rad Laboratories, Hercules, USA) antibodies (1:2500 dilution). Immunoreactive proteins were then visualized using the ECL+plus western blotting detection system (Amersham Biosciences, Buckinghamshire, England). Keratinocyte cell lysate (K) was used as a positive control. SF: synovial fluid; PS: patient serum.

Patient Samples

Synovial fluid was obtained from the knee joints of patients with active synovitis prior to the institution of anti-TNF therapeutics. All patients had a DAS score>6.0. Matched blood samples were obtained by standard venipuncture procedures. The clot was removed by centrifugation.

Recombinant 14-3-3 Eta cDNA for keratinocyte-derived 14-3-3 eta was prepared from total RNA extracted from human keratinocytes, cloned and expressed in *E. coli*, and affinity purified, following the methods described in Ghahary et al 2004 J Invest Dermatol 122:1188-1197. Primers used for PCR amplification of the 14-3-3 eta cDNA were SEQ ID NO: 15 (GCGAATTCCT-GCAGCGGGCGCGGCTGGCCGA) and SEQ ID NO: 16 (GCTCGAGCCTGAAGGATCTTCAGTTGCCTTC).

Example 1

14-3-3 Expression in Synovial Fluid and Serum of RA Affected Patients

Figure 2:
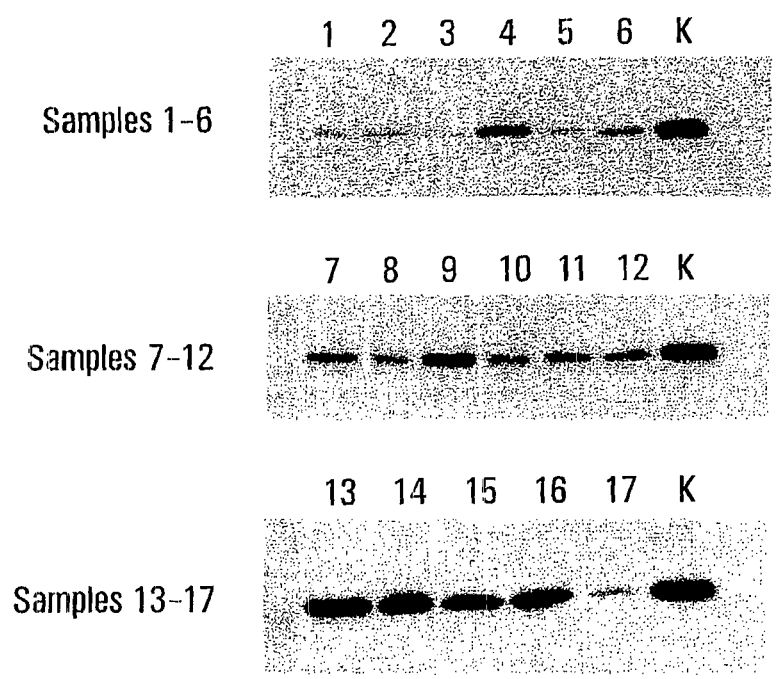

The levels of the different isoforms of 14-3-3 proteins—β, γ, ε, η, τ, σ, and ζ—in pooled patient synovial fluid (SF) and serum (PS) samples were analyzed by western analysis using keratinocyte cell lysate (K) as a positive control. Only the η and γ isoforms were detected in SF samples, and stained with greater intensity compared to PS. Articular joint synovial fluid samples from 17 RA patients who presented with active synovitis, but had not yet received anti-TNF therapies also exhibited consistent expression of the η isoform of 14-3-3 (FIG. 2). All patients had a disease activity score (DAS) greater than 6.0.

Example 2

MMP Expression in Patient Synovial Fluid Serum

Figure 3:
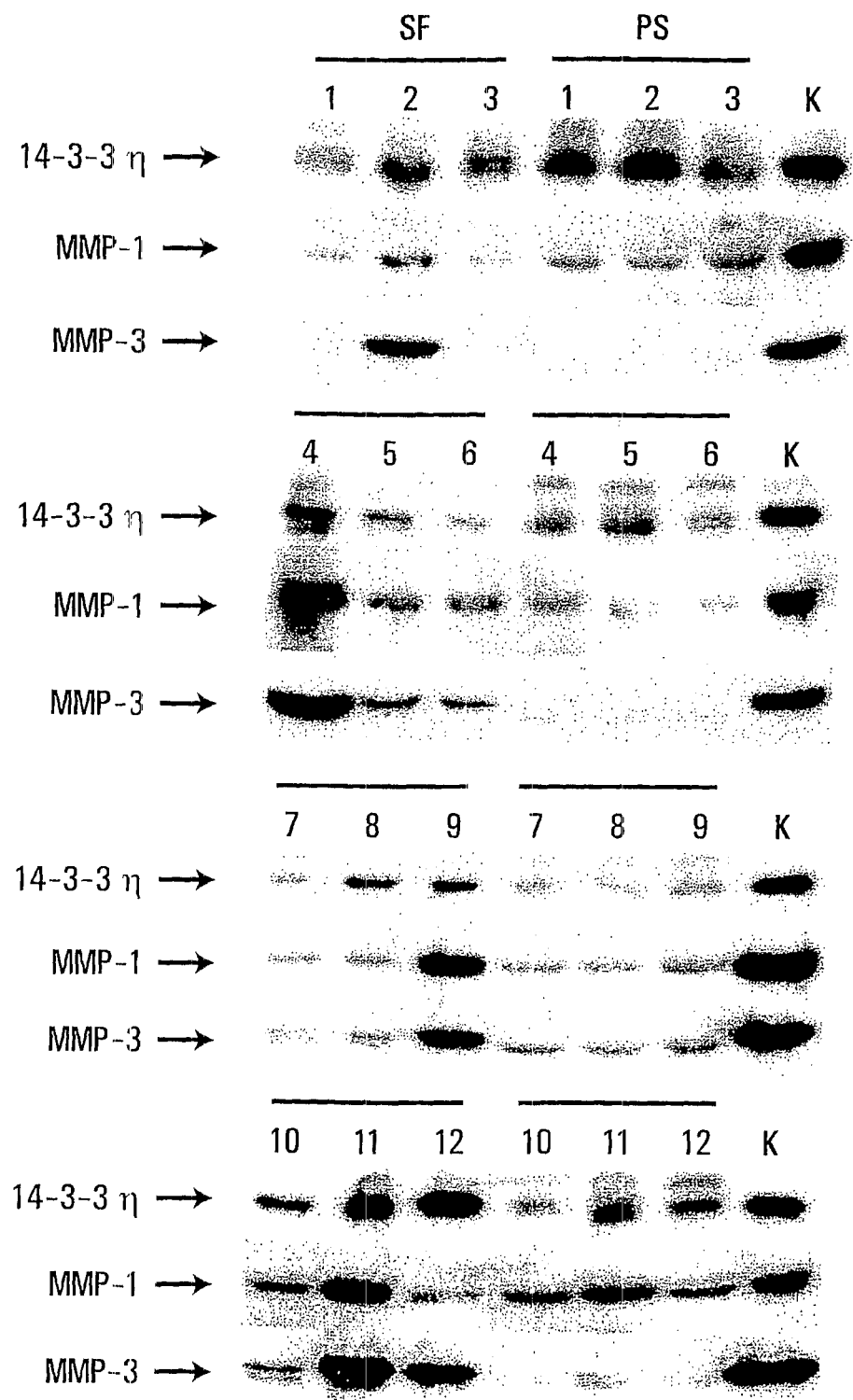
Figure 4:
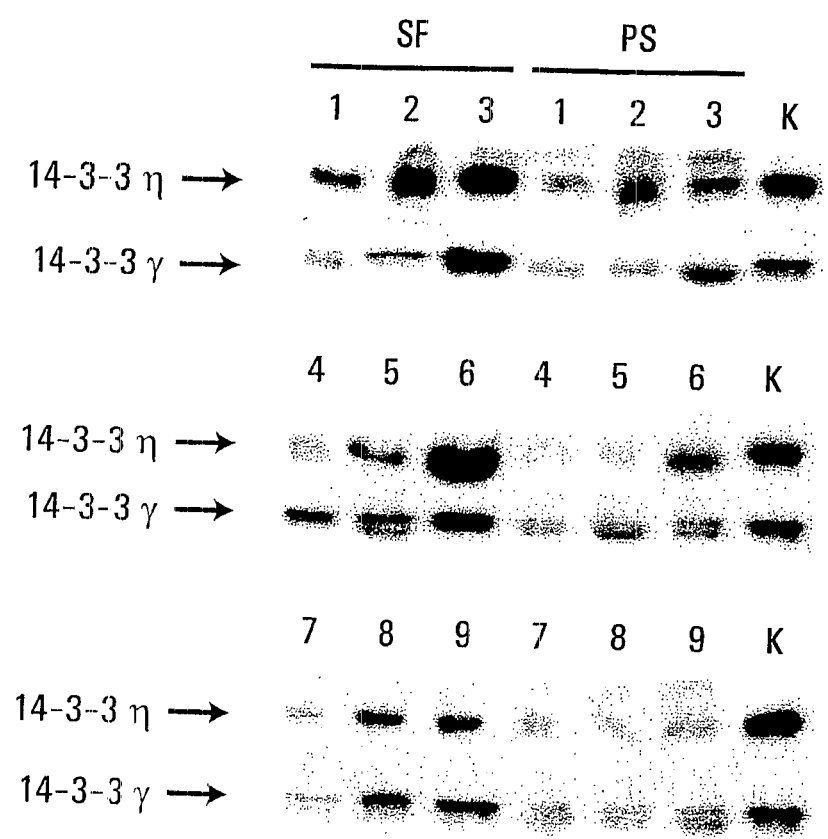
Figure 5:
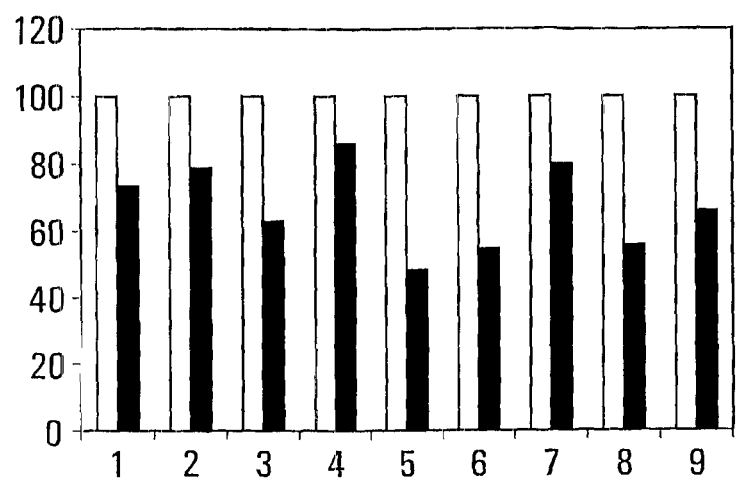

To determine if these variations were correlated to those of MMP-1 and MMP-3 in the same synovial samples, a total of 12 RA synovial fluid samples and their matched serum samples were simultaneously evaluated for 14-3-3 η and γ as well as for MMP-1 and MMP-3 proteins (FIG. 3). 14-3-3 η was detected in all samples. MMP-1 was detected in all samples, both SF and PS, while MMP-3 was more variable in the levels detected. The 14-3-3 γ isoform was also detected in patient synovial fluid and serum samples (FIG. 4, 5).

The expression of MMP-1 and MMP-3 demonstrate significant correlation with the expression of the 14-3-3 η and γ isoforms in both synovial fluid and serum (Table 1).

TABLE 1

Correlation of MMP and 14-3-3 protein levels in serum and synovial fluid

| | 14-3-3 η serum | 14-3-3 η synovium | 14-3-3 γ serum | 14-3-3 γ synovium |
|---|---|---|---|---|
| MMP-1 | r = 0.62; p = 0.02 | r = 0.83; p = 0.03 | r = 0.77; p = 0.02 | r = 0.65; p = 0.03 |
| MMP-3 | r = 0.68; p = 0.01 | r = 0.77; p = 0.003 | r = 0.80; p = 0.03 | r = 0.76; p = 0.04 |

Example 3

Figure 6A:
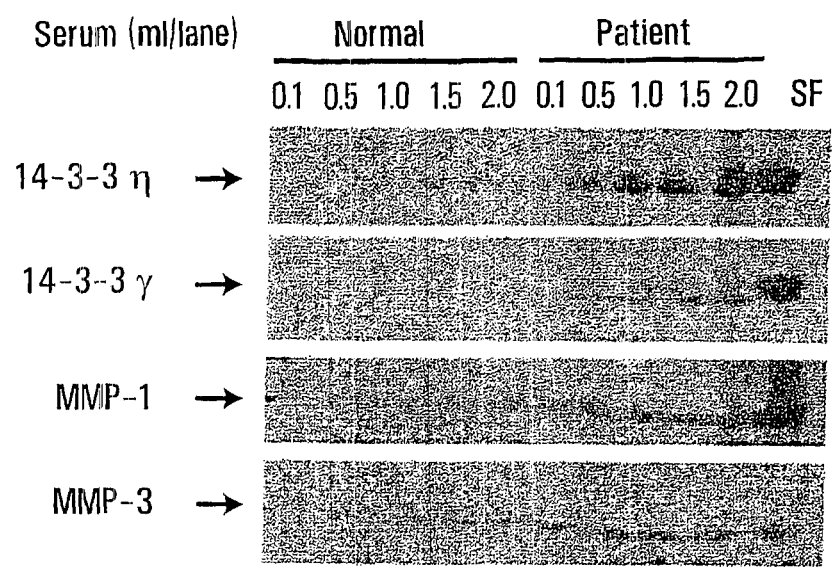

Sensitivity of Western Blot Detection of 14-3-3 Protein in Patient Serum and Synovial Fluid Samples To determine the detection level of 14-3-3 η in synovial fluid and serum samples, samples from 12 RA-affected or normal patients were pooled, and limiting dilutions of the pooled samples were analyzed by western blot. 14-3-3 η was detectable over a range of dilutions—as low as 0.1 µl effective volume of synovial fluid and 1.0 µl effective volume of serum (FIG. 6A).

Figure 6B:
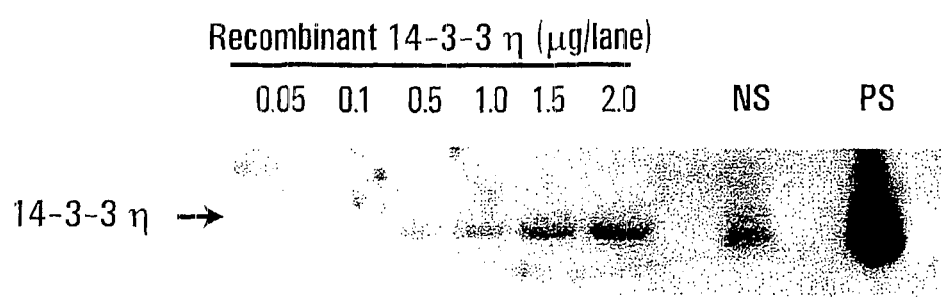

2 µl of pooled normal serum (NS) or patient serum (PS) was run alongside known concentrations of recombinant 14-3-3 η, ranging from 0.05-2.0 µg. The 2 µl volume of NS and PS samples was estimated to have approximately 1-1.5 and 15-20 μg of 14-3-3 η, respectively (FIG. 6B). This suggests that the level of 14-3-3 η occurs in about a 10-fold excess in the serum of RA affected patients, compared to normal patients.

Example 4

Detection of 14-3-3 η Before and after Anti-TNF Therapy

Figure 7:
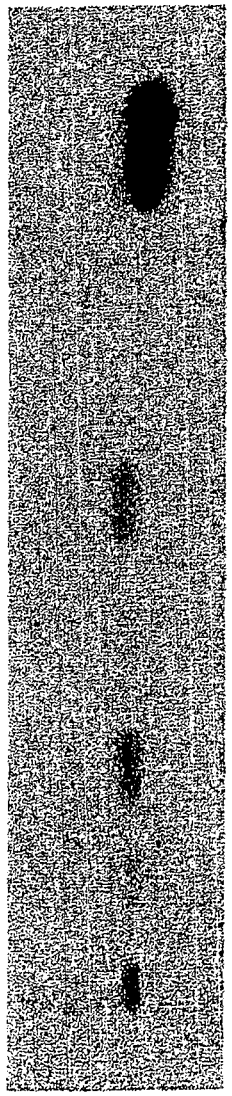

FIG. 7 illustrates the sequential detection of levels of 14-3-3 eta protein in 4 ml of serum samples from RA patients before (U) and after anti-TNF-a (T) Treatment. N=negative control which is 4 ml of a pooled serum sample prepared from 12 serum samples taken from 12 healthy individuals. P=positive control which is 4 mg of keratinocyte cell lysate total protein.

REFERENCES

The following documents are incorporated herein by reference:
1. Harris E D Jr., History and Epidemiology of Rheumatoid Arthritis: How long has it affected us, and who is at risk? In: Rheumatoid Arthritis. Philadelphia: W.B. Saunders Company, 1997: 21-27.
2. Harris E D Jr., Introduction. In: Rheumatoid Arthritis. Philadelphia: W.B. Saunders Company, 1997: xix-xxiii.
3. Harris E D Jr., Rheumatoid Synovium: Complex, and More Than the Sum of its Parts. In: Rheumatoid Arthritis. Philadelphia: W.B. Saunders Company, 1997: 127-149.
5. Firestein G S. (1997). Rheumatoid synovitis and pannus. In: J. H. Klippel and P. A. Dieppe, Editors, Rheumatology, Mosby, London, pp. 5/13.1-5/13.5, 1997.
6. Pap T, Shigeyama Y, Kuchen S. (2000). Arthritis Rheum. 43: 1226-1232.
7. Tolboom T C A, Pieterman E, van der Laan W E. Ann. Rheum. Dis. 61: 975-980, 2002.
8. Sorsa T, Konttinen Y T, Lindy O. Arthritis Rheum. 22: 44-53, 1992.
9. Lindy O, Konttinen Y T, Sorsa T. Arthritis Rheum. 40:1391-1399, 1997.
10. Ahrens D, Koch A E, Pope R M. Arthritis Rheum. 39:1576-1587, 1996.
11. Smeets T J M, Dayer J M, Karan M C. Arthritis Rheum. 43:270-274, 2000.
12. Poole A R; Cartilage in health and disease. In: Koopman W J. Ed. Arthritis and Allied conditions. A textbook of rheumatology. 14th ed. Baltimore: Williams and Wilikins, 2001: 226-284.
13. Konttinen Y T, Ceponis A, Takagi M, Ainola M, Sorsa T, Sutinen M, et al. Matrix Biol. 17:585-601, 1998.
14. Katrib. A, McNeil H P, Youssef P P: Inflamm. Res. 51: 170-175, 2002.
15. Harris E D Jr., Cytokines, Lymphokines, Growth Factors, and Chemokines. In: Rheumatoid Arthritis. Philadelphia: W.B. Saunders Company, 1997: 105-125.
16. Jasser, M. Z., Mitchell P. G. and Cheung, H. S.: induction of stomelysin-1 and collagenases synthesis in fibrochondrocytes by TNF-alpha. Matrix Biology 14: 241, 1994.
17. Burger D, Rezzonico R, Li J M, Modoux C, Pierce R A, Welgus H G, Dayer J M. Arthritis Rheum. 41(10):1748-59, 1998
18. Y. Yamamura, R. Gupta, Y. Morit, X. He, R. Pai, J. Endres, A. Freiberg, K. Chung and D. A. Fox. J. Immunol. 166 (2001), pp. 2270-2275
19. Miranda-Carus M E, Balsa A, Benito-Miguel M, Perez de Ayala C, Martin-Mola E. J. Immunol. 173:1463-1476, 2004
20. Cho M L, Yoon C H, Hwang C Y. Arthritis Rheum. 50:776-784, 2004
21. Bombara M P, Webb D L, Conrad P. J. Leukocyte Biol. 54: 399-406, 1993.
22. McInnes I B, Leung B P, Liew F Y. Arthritis Res. 2(5):374-8.34, 2000.
23. F U H, Subramanian R R, Masters S C: Annu Rev Pharmacol Toxicol 40:617-647, 2000.
24. Hsich G, Kenney K, Gibbs C J, Lee K H, Harrington M G: N Engl J Med 335:924-30, 1996
25. Wilker E, Yaffe M B: J Mol Cell Cardiol 37: 633-642, 2004.
26. Moore et al. 1967.
27. Ichimura T, Isobe T, Okuyama T, Yamauchi T, Fujisawa H (1987) FEBS Lett. 219:79-82.
28. Ichimura T, Isobe T, Okuyama T, Takahashi N, Araki K, Kuwano R, Akahashi Y (1988). Proc Natl Acad Sci USA, 85:7084-8.
29. Toker A, Ellis C A, Sellers L A, Atiken A 1990. Eur J Biochem 191:421-429.
30. Craparo A, Freund R, Gustafson T (1997). J Biol Chem 272:11663-69.
31. Yaffe M B (2002). FEBS Lett 513(1):53-57.
32. Hermeking H, Lengauer C, Polyak K, He T C, Zhang L, Thiagalingam S, Kinzler K W, Volgelstein B. Mol Cell 1:3-11, 1997.
33. Chan T A, Hermeking H, Lengauer C, Kinzler K W, Volgelstein B. Nature 401:616-620, 1999.
34. Laronga C, Yang H Y, Neal C, Lee M H (2000). J. Biol. Chem. 275:23106-23112.
35. Boston P F, Jackson P, Thompson R J. J. Neurochem. 38, 1475-82, 1982.
36. Katz A B, Taichman, L B. J Invest Dermatol 112:818-821, 1999.
37. Ghahary A, Karimi-Busheri F, Marcoux Y, Li Y, Tredget E E, Kilani R T, Li L, Zheng J, Karami A, Keller B, Weinfeld M. J. Invest. Dermatol. 122(5): 1188-1197, 2004.
38. Ghaffari A, Li Y, Karami A, Ghaffari M, Tredget E E, Ghahary A. J. Cell. Biochem. January 2006.

While specific embodiments of the invention have been described and illustrated, such embodiments should be considered illustrative of the invention only and not as limiting the invention as construed in accordance with the accompanying claims.

The invention claimed is:

1. A method for determining the efficacy of a therapeutic regimen in an arthritic patient, comprising:
   administering a therapeutic approach to a patient diagnosed with arthritis;
   obtaining a test biological sample from said patient, wherein said test sample is selected from the group consisting of blood, serum, plasma, and synovial fluid;
   detecting the presence or relative amount of the eta isoform of the 14-3-3 protein in the test sample; wherein said detection step comprises contacting the test sample with a non-human anti-human 14-3-3 protein antibody that is isoform specific for the 14-3-3 eta protein; and
   using the presence or relative amount of the 14-3-3 eta protein to establish the efficacy of the therapeutic regimen in said arthritic patient; wherein a decreased level of said 14-3-3 eta protein in said test sample in comparison with a previous sample from said patient is indicative of the efficacy of an ongoing therapeutic regimen.

2. The method according to claim 1, wherein said 14-3-3 eta isoform comprises the amino acid sequence of SEQ ID NO: 3.

3. The method according to claim 1, further comprising detection of at least one additional arthritis marker in said test sample useful for detecting and/or diagnosing arthritis in the test subject.

4. The method according to claim 3, wherein said at least one additional arthritis marker is a matrix metalloproteinase.

5. The method according to claim 1, wherein the arthritis is rheumatoid arthritis.

6. The method of claim 1, wherein the arthritis is early stage arthritis.

7. The method of claim 1, wherein the therapeutic approach is the use of non-steroidal anti-inflammatory medications (NSAIDs).

8. The method of claim 1, wherein the therapeutic approach consists of any one of the cyclooxygenase2 specific inhibitors (CSIs), glucocorticoids, disease-modifying anti-rheumatic drugs (DMARDs), anti-TNF alpha neutralizing agents and immunosuppressive or cytotoxic drugs.

9. A method of detecting the eta isoform of the 14-3-3 protein in a patient, said method comprising:
 a. obtaining a test sample from a patient at risk or suspected of having arthritis, wherein the test sample is selected from the group consisting of blood, serum, plasma, and synovial fluid; and
 b. detecting whether 14-3-3 eta protein is present in the test sample by contacting the test sample with an anti-14-3-3 eta protein antibody and detecting binding between 14-3-3 eta protein and the antibody.

* * * * *

SEQUENCE LISTING

<160> NUMBER OF SEQ ID NOS: 16

<210> SEQ ID NO 1
<211> LENGTH: 242
<212> TYPE: PRT

-continued

```
<213> ORGANISM: Homo sapiens
<220> FEATURE:
<223> OTHER INFORMATION: 14-3-3 beta protein; brain protein 14-3-3 beta
      isoform
<220> FEATURE:
<223> OTHER INFORMATION: Alternate nomenclature: Tyrosine
      3-monooxygenase/tryptophan 5-monooxygenase activation protein,
      beta isoform, YWHAB

<400> SEQUENCE: 1

Met Thr Met Asp Lys Ser Glu Leu Val Gln Lys Ala Lys Leu Ala Glu
1               5                   10                  15

Gln Ala Glu Arg Tyr Asp Asp Met Ala Ala Ala Met Lys Ala Val Thr
            20                  25                  30

Glu Gln Gly His Glu Leu Ser Asn Glu Glu Arg Asn Leu Leu Ser Val
        35                  40                  45

Ala Tyr Lys Asn Val Val Gly Ala Arg Arg Ser Ser Trp Arg Val Ile
    50                  55                  60

Ser Ser Ile Glu Gln Lys Thr Glu Arg Asn Glu Lys Lys Gln Gln Met
65                  70                  75                  80

Gly Lys Glu Tyr Arg Glu Lys Ile Glu Ala Glu Leu Gln Asp Ile Cys
                85                  90                  95

Asn Asp Val Leu Glu Leu Leu Asp Lys Tyr Leu Ile Pro Asn Ala Thr
            100                 105                 110

Gln Pro Glu Ser Lys Val Phe Tyr Leu Lys Met Lys Gly Asp Tyr Phe
        115                 120                 125

Arg Tyr Leu Ser Glu Val Ala Ser Gly Asp Asn Lys Gln Thr Thr Val
    130                 135                 140

Ser Asn Ser Gln Gln Ala Tyr Gln Glu Ala Phe Glu Ile Ser Lys Lys
145                 150                 155                 160

Glu Met Gln Pro Thr His Pro Ile Arg Leu Gly Leu Ala Leu Asn Phe
                165                 170                 175

Ser Val Phe Tyr Tyr Glu Ile Leu Asn Ser Pro Glu Lys Ala Cys Ser
            180                 185                 190

Leu Ala Lys Thr Ala Phe Asp Glu Ala Ile Ala Glu Leu Asp Thr Leu
        195                 200                 205

Asn Glu Glu Ser Tyr Lys Asp Ser Thr Leu Ile Met Gln Leu Leu Arg
    210                 215                 220

Asp Asn Leu Thr Leu Trp Thr Ser Glu Asn Gln Gly Asp Glu Gly Asp
225                 230                 235                 240

Ala Gly

<210> SEQ ID NO 2
<211> LENGTH: 246
<212> TYPE: PRT
<213> ORGANISM: Homo sapiens
<220> FEATURE:
<223> OTHER INFORMATION: 14-3-3 gamma protein
<220> FEATURE:
<223> OTHER INFORMATION: Alternate nomenclature: Tyrosine
      3-monooxygenase/tryptophan 5-monooxygenase activation protein,
      gamma isoform, YWHAG

<400> SEQUENCE: 2

Met Val Asp Pro Glu Gln Leu Val Gln Lys Ala Arg Leu Ala Glu Gln
1               5                   10                  15

Ala Glu Gly Tyr Asp Asp Met Ala Ala Ala Met Lys Asn Val Thr Glu
            20                  25                  30

Leu Asn Glu Pro Leu Ser Asn Glu Glu Arg Asn Leu Leu Ser Val Ala
```

```
                35                  40                  45
Tyr Lys Asn Val Val Gly Ala Arg Arg Ser Ser Trp Arg Val Ile Ser
 50                  55                  60

Ser Ile Glu Gln Lys Thr Ser Ala Asp Gly Asn Glu Lys Ile Glu Met
 65                  70                  75                  80

Val Arg Ala Tyr Arg Glu Lys Val Glu Lys Leu Glu Ala Val Cys
                 85                  90                  95

Gln Asp Val Leu Ser Leu Val Asp Asn Tyr Leu Tyr Lys Asn Cys Ser
                100                 105                 110

Glu Thr Gln Tyr Glu Arg Lys Asp Leu Tyr Leu Lys Met Lys Gly Asp
                115                 120                 125

Tyr Tyr Arg Tyr Leu Ala Glu Val Ala Thr Gly Glu Lys Arg Gly Asp
            130                 135                 140

Val Val Glu Ser Ser Glu Lys Ala Tyr Ser Glu Arg Glu Ile Ser Lys
145                 150                 155                 160

Glu His Met Gln Pro Thr His Pro Ile Arg Leu Gly Leu Ala Leu Asn
                    165                 170                 175

Tyr Ser Val Phe Tyr Tyr Glu Ile Gln Asn Ala Pro Glu Gln Ala Cys
                180                 185                 190

His Leu Ala Lys Thr Glu Phe Glu Asp Ala Ile Ala Glu Leu Asp Thr
                195                 200                 205

Leu Asn Glu Glu Ser Tyr Lys Asp Ser Thr Leu Ile Met Gln Leu Leu
    210                 215                 220

Arg Asp Asn Leu Thr Leu Trp Thr Ser Asp Gln Gln Asp Asp His Asp
225                 230                 235                 240

Gly Gly Glu Gly Asn Asn
                245

<210> SEQ ID NO 3
<211> LENGTH: 244
<212> TYPE: PRT
<213> ORGANISM: Homo sapiens
<220> FEATURE:
<223> OTHER INFORMATION: 14-3-3 eta protein
<220> FEATURE:
<223> OTHER INFORMATION: Alternate nomenclature: Tyrosine
      3-monooxygenase/tryptophan 5-monooxygenase activation protein,
      eta isoform, YWHAH;
<220> FEATURE:
<223> OTHER INFORMATION: brain protein 14-3-3, eta isoform tyrosine
      3-monooxygenase/tryptophan 5-monooxygenase activation
      protein 1; YWHA1

<400> SEQUENCE: 3

Met Gly Asp Arg Glu Gln Leu Leu Gln Arg Ala Arg Leu Ala Glu Gln
 1               5                  10                  15

Ala Glu Arg Tyr Asp Asp Met Ala Ser Ala Met Lys Ala Val Thr Glu
                 20                  25                  30

Leu Asn Glu Pro Leu Ser Asn Glu Asp Arg Asn Leu Leu Ser Val Ala
             35                  40                  45

Tyr Lys Asn Val Val Gly Ala Arg Arg Ser Ser Trp Arg Val Ile Ser
 50                  55                  60

Ser Ile Glu Gln Lys Thr Met Ala Asp Gly Asn Glu Lys Lys Leu Glu
 65                  70                  75                  80

Lys Val Lys Ala Tyr Arg Glu Lys Ile Glu Lys Glu Leu Glu Thr Val
                 85                  90                  95

Cys Asn Asp Val Leu Ser Leu Leu Asp Lys Phe Leu Ile Lys Asn Cys
                100                 105                 110
```

Asn Asp Phe Gln Tyr Glu Ser Lys Val Phe Tyr Leu Lys Met Lys Gly
        115                 120                 125

Asp Tyr Tyr Arg Tyr Leu Ala Glu Val Ala Ser Gly Glu Lys Lys Asn
    130                 135                 140

Ser Val Val Glu Ala Ser Glu Ala Ala Tyr Lys Glu Ala Phe Glu Ile
145                 150                 155                 160

Ser Lys Glu Gln Met Gln Pro Thr His Pro Ile Arg Leu Gly Leu Ala
                165                 170                 175

Leu Asn Phe Ser Val Phe Tyr Tyr Glu Ile Gln Asn Ala Pro Glu Gln
                180                 185                 190

Ala Cys Leu Leu Ala Lys Gln Ala Phe Asp Asp Ala Ile Ala Glu Leu
            195                 200                 205

Asp Thr Leu Asn Glu Asp Ser Tyr Lys Asp Ser Thr Leu Ile Met Gln
        210                 215                 220

Leu Leu Arg Asp Asn Leu Thr Leu Trp Thr Ser Asp Gln Gln Asp Glu
225                 230                 235                 240

Glu Ala Gly Glu

<210> SEQ ID NO 4
<211> LENGTH: 255
<212> TYPE: PRT
<213> ORGANISM: Homo sapiens
<220> FEATURE:
<223> OTHER INFORMATION: 14-3-3 epsilon protein
<220> FEATURE:
<223> OTHER INFORMATION: Alternate nomenclature: Tyrosine
      3-monooxygenase/tryptophan 5-monooxygenase activation protein,
      epsilon isoform, YWHAE epsilon isoform

<400> SEQUENCE: 4

Met Asp Asp Arg Glu Asp Leu Val Tyr Gln Ala Lys Leu Ala Glu Gln
1               5                   10                  15

Ala Glu Arg Tyr Asp Glu Met Val Glu Ser Met Lys Lys Val Ala Gly
            20                  25                  30

Met Asp Val Glu Leu Thr Val Glu Glu Arg Asn Leu Leu Ser Val Ala
        35                  40                  45

Tyr Lys Asn Val Ile Gly Ala Arg Arg Ala Ser Trp Arg Ile Ile Ser
    50                  55                  60

Ser Ile Glu Gln Lys Glu Glu Asn Lys Gly Gly Glu Asp Lys Leu Lys
65                  70                  75                  80

Met Ile Arg Glu Tyr Arg Gln Met Val Glu Thr Glu Leu Lys Leu Ile
                85                  90                  95

Cys Cys Asp Ile Leu Asp Val Leu Asp Lys His Leu Ile Pro Ala Ala
                100                 105                 110

Asn Thr Gly Glu Ser Lys Val Phe Tyr Tyr Lys Met Lys Gly Asp Tyr
            115                 120                 125

His Arg Tyr Leu Ala Glu Phe Ala Thr Gly Asn Asp Arg Lys Glu Ala
        130                 135                 140

Ala Glu Asn Ser Leu Val Ala Tyr Lys Ala Ala Ser Asp Ile Ala Met
145                 150                 155                 160

Thr Glu Leu Pro Pro Thr His Pro Ile Arg Leu Gly Leu Ala Leu Asn
                165                 170                 175

Phe Ser Val Phe Tyr Tyr Glu Ile Leu Asn Ser Pro Asp Arg Ala Cys
            180                 185                 190

Arg Leu Ala Lys Ala Ala Phe Asp Asp Ala Ile Ala Glu Leu Asp Thr
        195                 200                 205

```
Leu Ser Glu Glu Ser Tyr Lys Asp Ser Thr Leu Ile Met Gln Leu Leu
    210                 215                 220

Arg Asp Asn Leu Thr Leu Trp Thr Ser Asp Met Gln Gly Asp Gly Glu
225                 230                 235                 240

Glu Gln Asn Lys Glu Ala Leu Gln Asp Val Glu Asp Glu Asn Gln
                245                 250                 255

<210> SEQ ID NO 5
<211> LENGTH: 247
<212> TYPE: PRT
<213> ORGANISM: Homo sapiens
<220> FEATURE:
<223> OTHER INFORMATION: 14-3-3 sigma protein
<220> FEATURE:
<223> OTHER INFORMATION: Alternate nomenclature: stratifin

<400> SEQUENCE: 5

Met Glu Arg Ala Ser Leu Ile Gln Lys Ala Lys Leu Ala Glu Gln Ala
1               5                   10                  15

Glu Arg Tyr Glu Asp Met Ala Ala Phe Met Lys Gly Ala Val Glu Lys
                20                  25                  30

Gly Glu Glu Leu Ser Cys Glu Glu Arg Asn Leu Leu Ser Val Ala Tyr
            35                  40                  45

Lys Asn Val Val Gly Gly Gln Arg Ala Ala Trp Arg Val Leu Ser Ser
    50                  55                  60

Ile Glu Gln Lys Ser Asn Glu Glu Gly Ser Glu Glu Lys Gly Pro Glu
65                  70                  75                  80

Val Arg Glu Tyr Arg Glu Lys Val Glu Thr Glu Leu Gln Gly Val Cys
                85                  90                  95

Asp Thr Val Leu Gly Leu Leu Asp Ser His Leu Ile Lys Glu Ala Gly
                100                 105                 110

Asp Ala Glu Ser Arg Val Phe Tyr Leu Lys Met Lys Gly Asp Tyr Tyr
            115                 120                 125

Arg Tyr Leu Ala Glu Val Ala Thr Gly Asp Asp Lys Lys Arg Ile Ile
    130                 135                 140

Asp Ser Ala Arg Ser Ala Tyr Gln Glu Ala Met Asp Ile Ser Lys Lys
145                 150                 155                 160

Glu Met Pro Pro Thr Asn Pro Ile Arg Leu Gly Leu Ala Leu Asn Phe
                165                 170                 175

Ser Val Phe His Tyr Glu Ile Ala Asn Ser Pro Glu Glu Ala Ile Ser
            180                 185                 190

Leu Ala Lys Thr Thr Phe Asp Glu Ala Met Ala Asp Leu His Thr Leu
    195                 200                 205

Ser Glu Asp Ser Tyr Lys Asp Ser Thr Leu Ile Met Gln Leu Leu Arg
                210                 215                 220

Asp Asn Leu Thr Leu Trp Thr Ala Asp Asn Ala Gly Glu Glu Gly Gly
225                 230                 235                 240

Glu Ala Pro Gln Glu Pro Gln
                245

<210> SEQ ID NO 6
<211> LENGTH: 245
<212> TYPE: PRT
<213> ORGANISM: Homo sapiens
<220> FEATURE:
<223> OTHER INFORMATION: 14-3-3 tau protein
<220> FEATURE:
<223> OTHER INFORMATION: Alternate nomenclature: Tyrosine
```

3-monooxygenase/tryptophan 5-monooxygenase activation protein, tau
isoform, YWHAQ 14-3-3 protein, T-cell 14-3-3-theta HS1

<400> SEQUENCE: 6

```
Met Glu Lys Thr Glu Leu Ile Gln Lys Ala Lys Leu Ala Glu Gln Ala
1               5                   10                  15

Glu Arg Tyr Asp Asp Met Ala Thr Cys Met Lys Ala Val Thr Glu Gln
            20                  25                  30

Gly Ala Glu Leu Ser Asn Glu Glu Arg Asn Leu Leu Ser Val Ala Tyr
        35                  40                  45

Lys Asn Val Val Gly Arg Arg Ser Ala Trp Arg Val Ile Ser Ser
    50                  55                  60

Ile Glu Gln Lys Thr Asp Thr Ser Asp Lys Lys Leu Gln Leu Ile Lys
65                  70                  75                  80

Asp Tyr Arg Glu Lys Val Glu Ser Glu Leu Arg Ser Ile Cys Thr Thr
                85                  90                  95

Val Leu Glu Leu Leu Asp Lys Tyr Leu Ile Ala Asn Ala Thr Asn Pro
            100                 105                 110

Glu Ser Lys Val Phe Tyr Leu Lys Met Lys Gly Asp Tyr Phe Arg Tyr
        115                 120                 125

Leu Ala Glu Val Ala Cys Gly Asp Asp Arg Lys Gln Thr Ile Asp Asn
    130                 135                 140

Ser Gln Gly Ala Tyr Gln Glu Ala Phe Asp Ile Ser Lys Lys Glu Met
145                 150                 155                 160

Gln Pro Thr His Pro Ile Arg Leu Gly Leu Ala Leu Asn Phe Ser Val
                165                 170                 175

Phe Tyr Tyr Glu Ile Leu Asn Asn Pro Glu Leu Ala Cys Thr Leu Ala
            180                 185                 190

Lys Thr Ala Phe Asp Glu Ala Ile Ala Glu Leu Asp Thr Leu Asn Glu
        195                 200                 205

Asp Ser Tyr Lys Asp Ser Thr Leu Ile Met Gln Leu Leu Arg Asp Asn
    210                 215                 220

Leu Thr Leu Trp Thr Ser Asp Ser Ala Gly Glu Glu Cys Asp Ala Ala
225                 230                 235                 240

Glu Gly Ala Glu Asn
                245
```

<210> SEQ ID NO 7
<211> LENGTH: 245
<212> TYPE: PRT
<213> ORGANISM: Homo sapiens
<220> FEATURE:
<223> OTHER INFORMATION: 14-3-3 zeta protein
<220> FEATURE:
<223> OTHER INFORMATION: Alternate nomenclature: Tyrosine
    3-monooxygenase/tryptophan 5-monooxygenase activation protein,
    zeta isoform, YWHAZ; brain protein 14-3-3, zeta isoform

<400> SEQUENCE: 7

```
Met Asp Lys Asn Glu Leu Val Gln Lys Ala Lys Leu Ala Glu Gln Ala
1               5                   10                  15

Glu Arg Tyr Asp Asp Met Ala Ala Cys Met Lys Ser Val Thr Glu Gln
            20                  25                  30

Gly Ala Glu Leu Ser Asn Glu Glu Arg Asn Leu Leu Ser Val Ala Tyr
        35                  40                  45

Lys Asn Val Val Gly Ala Arg Arg Ser Ser Trp Arg Val Val Ser Ser
    50                  55                  60
```

```
Ile Glu Gln Lys Thr Glu Gly Ala Glu Lys Lys Gln Gln Met Ala Arg
 65                  70                  75                  80

Glu Tyr Arg Glu Lys Ile Glu Thr Glu Leu Arg Asp Ile Cys Asn Asp
                 85                  90                  95

Val Leu Ser Leu Leu Glu Lys Phe Leu Ile Pro Asn Ala Ser Gln Ala
            100                 105                 110

Glu Ser Lys Val Phe Tyr Leu Lys Met Lys Gly Asp Tyr Tyr Arg Tyr
        115                 120                 125

Leu Ala Glu Val Ala Ala Gly Asp Asp Lys Lys Gly Ile Val Asp Gln
    130                 135                 140

Ser Gln Gln Ala Tyr Gln Glu Ala Phe Glu Ile Ser Lys Lys Glu Met
145                 150                 155                 160

Gln Pro Thr His Pro Ile Arg Leu Gly Leu Ala Leu Asn Phe Ser Val
                165                 170                 175

Phe Tyr Tyr Glu Ile Leu Asn Ser Pro Glu Lys Ala Cys Ser Leu Ala
            180                 185                 190

Lys Thr Ala Phe Asp Glu Ala Ile Ala Glu Leu Asp Thr Leu Ser Glu
        195                 200                 205

Glu Ser Tyr Lys Asp Ser Thr Leu Ile Met Gln Leu Leu Arg Asp Asn
    210                 215                 220

Leu Thr Leu Trp Thr Ser Asp Thr Gln Gly Asp Glu Ala Glu Ala Gly
225                 230                 235                 240

Glu Gly Gly Glu Asn
                245

<210> SEQ ID NO 8
<211> LENGTH: 3015
<212> TYPE: DNA
<213> ORGANISM: Homo sapiens
<220> FEATURE:
<223> OTHER INFORMATION: 14-3-3 beta cDNA (NM_139323) 3015 nt

<400> SEQUENCE: 8
gcggaagtgg agctaccgcc accgccgccg ccgattccgg agccggggta gtcgccgccg      60
ccgccgccgc tgcagccact gcaggcaccg ctgccgccgc tgagtagtg ggcttaggaa      120 ggaagaggtc atctcgctcg gagcttcgct cggaagggtc tttgttccct gcagccctcc    180
cacgggaatg acaatggata aagtgagct ggtacagaaa gccaaactcg ctgagcaggc      240
tgagcgatat gatgatatgg ctgcagccat gaaggcagtc acagaacagg ggcatgaact     300
ctccaacgaa gagagaaatc tgctctctgt tgcctacaag aatgtggtag cgcccgccg      360 ctcttcctgg cgtgtcatct ccagcattga gcagaaaaca gagaggaatg agaagaagca    420
gcagatgggc aaagagtacc gtgagaagat agaggcagaa ctgcaggaca tctgcaatga    480
tgttctggag ctgttggaca atatcttat tcccaatgct acacaaccag aaagtaaggt     540
gttctacttg aaaatgaaag gagattattt taggtatctt tctgaagtgg catctgagag   600
caacaaacaa accactgtgt cgaactccca gcaggcttac caggaagcat ttgaaattag     660
taagaaagaa atgcagccta cacacccaat tcgtcttggt ctggcactaa atttctcagt   720
cttttactat gagattctaa actctcctga aaaggcctgt agcctggcaa aacggcatt     780 tgatgaagca attgctgaat ggatacgct gaatgaagag tcttataaag acagcactct     840
gatcatgcag ttacttaggg acaatctcac tctgtggaca tcggaaaacc agggagacga    900
aggagacgct ggggagggag agaactaatg tttctcgtgc tttgtgatct gttcagtgtc   960
actctgtacc ctcaacatat atcccttgtg cgataaaaaa aaaaaaaaaa aaaaaagag    1020
```

```
aatcgtacgt cgactttcga tttttcacag cctcagccta ggaaaaatgg ttcatgggat    1080
aaacagctgg tatttgtatc taaaactcag attggtcaca taaatgccac ggcattccga    1140
agttttgatt ttgattaaca ttgacaggat tactgtgtgt ttaatttttt aaaaactgaa    1200
cactgtgatt atggggtttt gtaatttagc agaactctta ctggtagaaa aaatagacct    1260
gaattatgtg taacttttig gaaggtttaa tctgatatca aataatcat tgaaatacaa     1320 ttccattgta aagttgtaca gaaagttata gagattatat tgtgatgctg aacttggag     1380 tgagacacac atcatttggc atttgagttg aatggtaatt cacagtaatg ctgccgttgt    1440
tcgggactta aagacacttg acctgtttgg gctgttgcca cttaaaagtt catgaccaca    1500
aatgtccaca gtgtcttcct ctgaggaaac tcgaatcctg aaatggaaat tctttgtggc    1560
agataactgg cttatgacac cttgaaaagt tcaagtgctc atataacaca ccacactgaa    1620 cccccttttcc tacagcaata tgttcactat gttaccaatt gcaacttgt gcttcaatag    1680 tggaatctac tttcattgtt aacactgagc taaagaaaaa aagccgtgtg ttttatgaat    1740
gaccttatct gtttcctgga taatacccttt aagaataatg tcctgagtca ggcgtggtgg   1800
tgcgtgcatc tagtcccaac tatttgggag gctgaggcag gaggatcgct tgagcccagg    1860
agtttaaagc tgcagtgccc tgtggttgca cctgtgaata actgcactcc agcctgggca    1920
acatagcgag acctcatctc caaaaaagaa aacaaaaaac aaaaaaagga atgatgttct    1980
gtagagatgg cctttcactt gaggagtact cagttttcag gttcttccta gctcggggct    2040
tttaaatttt gaaatctaaa cattctttcc caccatcctt tttgactgtt gaccttggtt    2100
ttctcttcta agttctgtc cctctgcttc cttacttttt ttcctttttg aattctatct      2160
ttatctgtct tttgttcact ttttaatgct atatatgggc aggggtgaga gacattactg    2220
agcaccttgg tgagcaagcc tggctttaaa gattggagaa gagcttctgg caccagaacc    2280
ctgtcttcct ccagttctca acacggtgtt gctcttcagt catacccgaa tctgaatcaa    2340
aaaagtattt ttaaatatcc atgatttctc cctgtattga ggctagccct gatcatgctt    2400
tttgtgcctg tcaccaggtc tcccaagtgc actcatccag gtcagtgctc agatgtgttt    2460
aaggagaccc tatattcagg gaagttgcgt gaacactgca gtggggagaa ttgagaatag    2520
tcaggcctat cagtctcaca gaatcacccc tctacctttg atattccact agctgtaga    2580 gtccatctgt ttgtccatct gctgaaatga gaaagaaaa atttatgcac tgatttaaaa    2640
caaaccaaaa aaaagaaaa aaacaaaaaa aaaatccct cctttctagc tgaacaaaaa     2700
tgtgcagtta atacttggcg cttgaaaatg cagtagtgaa tgtggaacca agcctgtctg    2760
tatatctggt agctctttc ttgctttgtt ttttcttacc agtattctgc ctaacgtttg    2820
cttctgtgat ggttatattg cctagcaagc acacccgtgg ttgtgaaaat agtatagcaa    2880
aaaagaaaaa tccccggtta ttgatgtact agatttgtgt atgtctttta aacagttcta    2940 gtttcaccttt acacagaata atcaggaaaa gtgtaaaaat tcaaaagtga aataaaaatt    3000
ttatcagtta aaaaa                                                      3015
```

<210> SEQ ID NO 9
<211> LENGTH: 3747
<212> TYPE: DNA
<213> ORGANISM: Homo sapiens
<220> FEATURE:
<223> OTHER INFORMATION: 14-3-3 gamma cDNA (NM_012479) 3747 nt

<400> SEQUENCE: 9

-continued

| | |
|---|---|
| cagcagccgc agccgcctcg cgcccggtcc cgcggtcgca gctccagccg cctcctccgc | 60 |
| gcagccgccg cctcagctgc tcgctctgtg ggtcggtcct ctccggcact tgggctccag | 120 |
| tcgcgccctc caagcccttc aggccgcccc agtgtcctcc tccttctccg gccagaccca | 180 |
| gccccgcgaa gatggtggac cgcgagcaac tggtgcagaa agcccggctg gccgagcagg | 240 |
| cggagcgcta cgacgacatg gccgcggcca tgaagaacgt gacagagctg aatgagccac | 300 |
| tgtcgaatga ggaacgaaac cttctgtctg tggcctacaa gaacgttgtg ggggcacgcc | 360 |
| gctcttcctg gagggtcatc agtagcattg agcagaagac atctgcagac ggcaatgaga | 420 |
| agaagattga gatggtccgt gcgtaccggg agaagataga gaaggagttg gaggctgtgt | 480 |
| gccaggatgt gctgagcctg ctggataact acctgatcaa gaattgcagc gagacccagt | 540 |
| acgagagcaa agtgttctac ctgaagatga aggggactac taccgctac ctggctgaag | 600 |
| tggccaccgg agagaaaagg gcgacggtgg tggagtcctc cgagaaggcc tacagcgaag | 660 |
| cccacgagat cagcaaagag cacatgcagc ccacccaccc catccgatta ggcctggctc | 720 |
| ttaactactc cgtcttctac tatgagatcc agaacgcccc agagcaagcg tgccacttgg | 780 |
| ccaagaccgc gttcgacgac gccatcgccg agcttgacac cctcaacgag gactcctaca | 840 |
| aggactccac gctcatcatg cagctcctcc gcgacaacct cacgctctgg acgagcgacc | 900 |
| agcaggacga cgatggcggc gaaggcaaca attaaggccc caggggaact ggcagcgcac | 960 |
| gcggatgcta ctactgcagt ctttatttt tcccatgag ttgggggtcg ggtggggag | 1020 |
| ggaaagggag ggatgacctt cccagggaga aacccacgac ctgtcctgtc tttgatcgcc | 1080 |
| tctttgacat ttttgccaaa ataccactag tggaaagtca ggctagctgt gctggtattg | 1140 |
| gaatagcagc ctcacactgg cgtctggact gttctgtaga ttcatgcaag tggagctgtc | 1200 |
| tgtctctaat ttaacttatt gctagataat agggttttca gatgaaaaga aaacttaaag | 1260 |
| aggaatggcc ctcattcagt aagttctgtg gttccagtaa ggattttat gtacatacgc | 1320 |
| tctcgtctct cgttttgggt actttctatc tcatctgtct cggctctgca tgttttccag | 1380 |
| ggtgtagcct acagacatgg aacagtgtaa atcccagact gacagactta gaacctgagg | 1440 |
| tctcattcat cctatggtt taggccttgc cagttttccg aagtctctga ttagttgaca | 1500 |
| gtattaacac taaattgcag tttacagtat ttctacatta cagccatatg taacatcaag | 1560 |
| ccatcgattg tgtactttc ctttgctagt tgtttgggct ttaacatcct tattcagcct | 1620 |
| tatccaggtt ggttttgctg ttgatcggtc tcctaggcta aatgagaatg aaagcgactt | 1680 |
| caggttttg gttcataggt gctcggcagg tggctgtggg atttttttt tttttggtcc | 1740 |
| ttctttcctc ttaacgtaaa tccaccacca aaattattaa tcctcttgag agaaacgtga | 1800 |
| aacgccacaa aaatagagaa aattcaggtc tgtatgtcat ggatcgtgtt ggtattttca | 1860 |
| gagaacatcc cgcttctgaa gctgctgcag ctccctcctc agggatcaca ctgccgtcac | 1920 |
| ccactctgca ctggggcgtt tcctactgcg cctcgtgctg gcggacgcag ctgggtgcag | 1980 |
| aagctgtggg gtcggagagg cgtttggaga aggtctgtgg tgcagtgtgt gaaaattcag | 2040 |
| gtgctagaag cctactggta gaaaaaccca aaaggaagag ctatatcctt aaccattctg | 2100 |
| tccaatttcg ggagccttgt cagtgtgtca gttttcctc cccgaagaca ctccttcccc | 2160 |
| aagtaattgt aggaagataa aaaaactgtt accagataac aaacactgaa ctcctatttg | 2220 |
| accagaactt tttcctctcg agatagtttt ttcttttaa tgaaaaagc ataggaattg | 2280 |
| gagattggct tgtctcacgc agccagtgca catttggaat tgacgaaaac aacgttgcta | 2340 |
| tttccaccca tttgttttcg gcagccttaa ggccctcatt ctcatttcgg gtgaatctgt | 2400 |

```
ctatctgtga acgtggcccg catgtgcatt cttttttta tatatataaa gtcagtgacg      2460
aggaactccc gagacgtgta atgacaccac acttgttttc tttgtttctt tgttttattt      2520
aggcaagaag aggtgtgagt aattgaggaa aaactgacag atgcttttgc taataccaaa      2580
attgagctta caattaggaa ctgagtatgt gtaacaggat acaggtgaca gtgaagatag      2640
aagaaccacg atgaccacag actcaatgtg ctctgtaaca tcgcacagtt tacccagcat      2700
gactttcctt aggaggcccc ctcctcacgc tagagtaaaa gtcccagtta agtgaagcct      2760
accagaagaa ctagtagaag aagctttgcc gcttttgtgc ctctcacagg cgcctaaagt      2820
cattgccatg ggaggaagac gatttggggg gggaggggg gggcagggta ggtgggcttt      2880
tccctaattt atcttcatgt ccagtgagca gtgttgcgtt tttccttgta gcatttggaa      2940
atgatttact ggaattacaa aacctatttt tcctttaaat ttcagctttg gctctggctg      3000 cttttagaa taatgcaaga taaaaatcac acctgagggc tgaaaacgga gagggaatgg       3060
gagacttgat atttaagcag cttgaatggt ttttcttttc tttattttta aagaaatgca      3120
cttgcctatg atactgtctc tccagtgaaa tgattactcc tccattactc tattgataca      3180
atattgtgca tgctagtgtt gtatttctat acagtagctt gaaattgatt aacttatact      3240
gtaggtgtta tgtattccta tgacaaaaaa aattaagtct tcaaattttt taaaggtttt      3300 tttttttaa tttaattttt cctttggg gtaaagtttg ctctaccaaa tagtgattgt        3360
aacaaattga tctgtttgg atgttgctat agtgacatgc agttatatat tttgtttta        3420 aaagggggg agcaaaagaa acaccagtgt tagcttaatc ttaatgtctg gtgtttgtca       3480
tggtgaaatt ataactatta cagtgttgga gaacaacaaa tatgttctct gaatgagcct      3540
ttgtgctttt tgtcatgtta tgcagtgaac tattttaag gtctaatcag tgattatttt       3600
tccagctccg tgtttctcta aggaattatt tcacacacgg accatcttta gcagtttcct      3660
cagtgatgga atatcatgaa tgtgagtcat tatgtagctg tcgtacattg agcaaataaa      3720
cttacagatc tgaaaaaaaa aaaaaaa                                          3747

<210> SEQ ID NO 10
<211> LENGTH: 1810
<212> TYPE: DNA
<213> ORGANISM: Homo sapiens
<220> FEATURE:
<223> OTHER INFORMATION: 14-3-3 epsilon cDNA (NM_006761) 1810 nt

<400> SEQUENCE: 10
cggattgagg cgccgccatt tttgctgccc ggacgcggag cgagaggctg agagagtcgg        60
agacactatc cgcttccatc cgtcgcgcag accctgccgg agccgctgcc gctatggatg       120
atcgagagga tctggtgtac caggcgaagc tggccgagca ggctgagcga tacgacgaaa       180
tggtggagtc aatgaagaaa gtagcaggga tggatgtgga gctgacagtt gaagaaagaa       240
acctcctatc tgttgcatat aagaatgtga ttggagctag aagagcctcc tggagaataa       300
tcagcagcat tgaacagaaa gaagaaaaca agggaggaga agacaagcta aaaatgattc       360
gggaatatcg gcaaatggtt gagactgagc taaagttaat ctgttgtgac attctggatg       420
tactggacaa acacctcatt ccagcagcta acactgcgca gtccaaggtt ttctattata       480
aaatgaaagg ggactaccac aggtatctgg cagaatttgc cacaggaaac gacaggaagg       540
aggctgcgga gaacagccta gtggcttata agctgctag tgatattgca atgacagaac       600
ttccaccaac gcatcctatt cgcttaggtc ttgctctcaa ttttccgta ttctactacg        660
```

| | |
|---|---|
| aaattcttaa ttcccctgac cgtgcctgca ggttggcaaa agcagctttt gatgatgcaa | 720 |
| ttgcagaact ggatacgctg agtgaagaaa gctataagga ctctacactt atcatgcagt | 780 |
| tgttacgtga taatctgaca ctatggactt cagacatgca gggtgacggt gaagagcaga | 840 |
| ataaagaagc gctgcaggac gtggaagacg aaaatcagtg agacataagc caacaagaga | 900 |
| aaccatctct gaccaccccc tcctccccat cccacccttt ggaaactccc cattgtcact | 960 |
| gagaaccacc aaatctgact tttacatttg gtctcagaat ttaggttcct gccctgttgg | 1020 |
| tttttttttt tttttttttt aaacagtttt caaaagttct taaaggcaag agtgaatttc | 1080 |
| tgtggatttt actggtccca gcttttaggt tctttaagac actaacagga ctacatagag | 1140 |
| gcttttcag cattactgtg tcgtctccgt gccagatgtg gcaagatcac cattagcaaa | 1200 |
| tggaaattac atttgaaagc cattagactt ataggtgatg caagcatcta agagagaggt | 1260 |
| taatcacact atagaggcat aagtggtatc agttttcatt tttctaattg tttaaactgt | 1320 |
| gttttatacc agtgtttgca agtaattggg tgttagcttg agatggttaa aggtggtttg | 1380 |
| gggagggact tcgttgtaat ggttttgctg taaaaaatgt ttccaactcc gctgaaatgt | 1440 |
| tgctgaaaag catggtgctg gtaacagttc aacaatccgt ggctgctcat tcttgcctac | 1500 |
| tttactctcc cactgaagca ggttagcgtt gaaggtggta tggaaaagcc tgcatgcctg | 1560 |
| ttcaattctt tgtttcttc tccttccccc tcccctacc tccttcccct cactcctccc | 1620 |
| ctccttcgct cgctcaacct cttttgttca gtatgtgtaa cttgaagcta atttgtacta | 1680 |
| ctggatatct gactggagcc acagatacag aatctgtatt gttcttactg aaacacagca | 1740 |
| tggaattaac attaaactta aataaaacaa acctaaatta aaaaaaaaa aaaaaaaaa | 1800 |
| aaaaaaaaaa | 1810 |

<210> SEQ ID NO 11
<211> LENGTH: 1807
<212> TYPE: DNA
<213> ORGANISM: Homo sapiens
<220> FEATURE:
<223> OTHER INFORMATION: 14-3-3 eta cDNA (NM_003405) 1807 nt

<400> SEQUENCE: 11

| | |
|---|---|
| gcggccgcgt ctcctccctc ggcgttgtcc gcggcgcgag ccacagcgcg cggggcgagc | 60 |
| cagcgagagg gcgcgagcgg cggcgctgcc tgcagcctgc agcctgcagc ctccggccgg | 120 |
| ccggcgagcc agtgcgcgtg cgcggcggcg gcctccgcag cgaccgggga gcggactgac | 180 |
| cggcgggagg gctagcgagc cagcggtgtg aggcgcgagg cgaggccgag ccgcgagcga | 240 |
| catgggggac cgggagcagc tgctgcagcg ggcgcggctg gccgagcagg cggagcgcta | 300 |
| cgacgacatg gcctccgcta tgaaggcggt gacagagctg aatgaacctc tctccaatga | 360 |
| agatcgaaat ctcctctctg tggcctacaa gaatgtggtt ggtgccaggc gatcttcctg | 420 |
| gagggtcatt agcagcattg agcagaaaac catggctgat ggaaacgaaa agaaattgga | 480 |
| gaaagttaaa gcttaccggg agaagattga aaggagctg gagacagttt gcaatgatgt | 540 |
| cctgtctctg cttgacaagt tcctgatcaa gaactgcaat gatttccagt atgagagcaa | 600 |
| ggtgttttac ctgaaaatga ggggtgatta ctaccgctac ttagcagagg tcgcttctgg | 660 |
| ggagaagaaa aacagtgtgg tcgaagcttc tgaagctgcc tacaaggaag ccttttgaaat | 720 |
| cagcaaagag cagatgcaac ccacgcatcc catccggctg ggcctggccc tcaacttctc | 780 |
| cgtgttctac tatgagatcc agaatgcacc tgagcaagcc tgcctcttag ccaaacaagc | 840 |
| cttcgatgat gccatagctg agctggacac actaaacgag gattcctata aggactccac | 900 |

```
gctgatcatg cagttgctgc gagacaacct caccctctgg acgagcgacc agcaggatga      960
agaagcagga gaaggcaact gaagatcctt caggtcccct ggcccttcct tcacccacca     1020
cccccatcat caccgattct tccttgccac aatcactaaa tatctagtgc taaacctatc     1080
tgtattggca gcacagctac tcagatctgc actcctgtct cttgggaagc agtttcagat     1140
aaatcatggg cattgctgga ctgatggttg ctttgagccc acaggagctc ccttttgaa      1200 ttgtgtggag aagtgtgttc tgatgaggca ttttactatg cctgttgatc tatgggaaat     1260
ctaggcgaaa gtaatgggga agattagaaa gaattagcca accaggctac agttgatatt     1320
taaaagatcc atttaaaaca agctgatagt gtttcgttaa gcagtacatc ttgtgcatgc     1380
aaaaatgaat tcacccctcc cacctctttc ttcaattaat ggaaaactgt taagggaagc     1440
tgatacagag agacaacttg ctcctttcca tcagctttat aataaactgt ttaacgtgag     1500
gtttcagtag ctccttggtt ttgcctcttt aaattatgac gtgcacaaac cttcttttca     1560
atgcaatgca tctgaaagtt ttgatacttg taactttttt ttttttttgg ttgcaattgt     1620
ttaagaatca tggatttatt ttttgtaact ctttggctat tgtccttgtg tatcctgaca     1680
gcgccatgtg tgtcagccca tgtcaatcaa gatgggtgat tatgaaatgc agacttcta     1740 aaataaatgt tttggaattc aatgggtaaa taaatgctgc tttggggata ttaaaaaaaa     1800
aaaaaaa                                                               1807

<210> SEQ ID NO 12
<211> LENGTH: 2166
<212> TYPE: DNA
<213> ORGANISM: Homo sapiens
<220> FEATURE:
<223> OTHER INFORMATION: 14-3-3 tau cDNA (NM_006826) 2166 nt

<400> SEQUENCE: 12
gtggtgggac tcgcgtcgcg gccgcggaga cgtgaagctc tcgaggctcc tcccgctgcg       60
ggtcggcgct cgccctcgct ctcctcgccc tccgccccgg ccccggcccc gcgcccgcca      120
tggagaagac tgagctgatc cagaaggcca agctggccga gcaggccgag cgctacgacg      180
acatggccac ctgcatgaag gcagtgaccg agcagggcgc cgagctgtcc aacgaggagc      240
gcaacctgct ctccgtggcc tacaagaacg tggtcggggg ccgcaggtcc gcctggaggg      300
tcatctctag catcgagcag aagaccgaca cctccgacaa gaagttgcag ctgattaagg      360
actatcggga gaaagtggag tccgagctga gatccatctg caccacggtg ctggaattgt      420
tggataaata tttaatagcc aatgcaacta atccagagag taaggtcttc tatctgaaaa      480
tgaagggtga ttacttccgg taccttgctg aagttgcgtg tggtgatgat cgaaaacaaa      540
cgatagataa ttcccaagga gcttaccaag aggcatttga tataagcaag aaagagatgc      600
aacccacaca cccaatccgc ctggggcttg ctcttaactt ttctgtattt tactatgaga      660
ttcttaataa cccagagctt gcctgcacgc tggctaaaac ggcttttgat gaggccattg      720
ctgaacttga tacactgaat gaagactcat acaaagacag caccctcatc atgcagttgc      780
ttagagacaa cctaacactt tggacatcag acagtgcagg agaagaatgt gatgcggcag      840
aaggggctga aaactaaatc catacagggt gtcatccttc tttccttcaa gaaacctttt      900
tacacatctc cattccttat tccacttgga tttcctatag caagaaaacc cattcatgtg      960
tatgaaatca actgtttata gtcttttcac actgcagctt tgggaaaact tcattccttg     1020
atttgtgttt gtcttggcct tcctggtgtg cagtactgct gtagaaaagt attaatagct     1080
```

| | |
|---|---|
| tcatttcata taaacataag taactcccaa acacttatgt agaggactaa aaatgtatct | 1140 |
| ggtatttaag taatctgaac cagttctgca agtgactgtg ttttgtatta ctgtgaaaat | 1200 |
| aagaaaatgt agttaattac aatttaaaga gtattccaca taacttctta atttctacat | 1260 |
| tccctccctt actcttcggg ggtttccttt cagtaagcaa cttttccatg ctcttaatgt | 1320 |
| attccttttt agtaggaatc cggaagtatt agattgaatg gaaaagcact tgccatctct | 1380 |
| gtctaggggt cacaaattga aatggctcct gtatcacata cggaggtctt gtgtatctgt | 1440 |
| ggcaacaggg agtttcctta ttcactcttt atttgctgct gtttaagttg ccaacctccc | 1500 |
| ctcccaataa aaattcactt acacctcctg cctttgtagt tctggtattc actttactat | 1560 |
| gtgatagaag tagcatgttg ctgccagaat acaagcattg cttttggcaa attaaagtgc | 1620 |
| atgtcatttc ttaatacact agaaagggga aataaattaa agtacacaag tccaagtcta | 1680 |
| aaactttagt acttttccat gcagatttgt gcacatgtga gagggtgtcc agtttgtcta | 1740 |
| gtgattgtta tttagagagt tggaccacta ttgtgtgttg ctaatcattg actgtagtcc | 1800 |
| caaaaagcc ttgtgaaaat gttatgccct atgtaacagc agagtaacat aaaataaaag | 1860 |
| tacatttat aaaccattta ctatggcttt gtaacaattg catacccata ttttaaggga | 1920 |
| caggtgaatt tactactttc taaagtttat tgatacttcc cttttatgta aaatgtagta | 1980 |
| gtgataccta tatttccaca ttgtgcattg tgacacactt gtctagggat gcctggaagt | 2040 |
| gtataaaatt ggactgcatt tcttagagtg ttttactata gatcagtctc atgggccatc | 2100 |
| tcttcctcag atgtaaatga tatctggtta agtgttatat ggaataaagt ggacatttta | 2160 |
| aaacta | 2166 |

<210> SEQ ID NO 13
<211> LENGTH: 1329
<212> TYPE: DNA
<213> ORGANISM: Homo sapiens
<220> FEATURE:
<223> OTHER INFORMATION: 14-3-3 sigma cDNA (NM_006142) 1336 nt

<400> SEQUENCE: 13

| | |
|---|---|
| gagagacaca gagtccggca ttggtcccag gcagcagtta gcccgccgcc cgcctgtgtg | 60 |
| tccccagagc catggagaga gccagtctga tccagaaggc caagctggca gagcaggccg | 120 |
| aacgctatga ggacatggca gccttcatga aaggcgccgt ggagaagggc gaggagctct | 180 |
| cctgcgaaga gcgaaacctg ctctcagtag cctataagaa cgtggtgggc ggccagaggg | 240 |
| ctgcctggag ggtgctgtcc agtattgagc agaaaagcaa cgaggagggc tcggaggaga | 300 |
| aggggcccga ggtgcgtgag taccgggaga aggtggagac tgagctccag ggcgtgtgcg | 360 |
| acaccgtgct gggcctgctg gacagccacc tcatcaagga ggccggggac gccgagagcc | 420 |
| gggtcttcta cctgaagatg aagggtgact actaccgcta cctggccgag gtggccaccg | 480 |
| gtgacgacaa gaagcgcatc attgactcag cccggtcagc ctaccaggag gccatggaca | 540 |
| tcagcaagaa ggagatgccg cccaccaacc ccatccgcct gggcctggcc ctgaactttt | 600 |
| ccgtcttcca ctacgagatc gccaacagcc ccgaggaggc catctctctg gccaagacca | 660 |
| cttttgacga ggccatggct gatctgcaca cccctcagcga ggactcctac aaagacagca | 720 |
| ccctcatcat gcagctgctg cgagacaacc tgacactgtg gacggccgac aacgccgggg | 780 |
| aagaggggg cgaggctccc caggagcccc agagctgagt gttgcccgcc accgccccgc | 840 |
| cctgcccccct ccagtccccc accctgccga gaggactagt atgggtgggg aggcccacc | 900 |
| cttctcccct aggcgctgtt cttgctccaa agggctccgt ggagagggac tggcagagct | 960 |

```
gaggccacct ggggctgggg atcccactct tcttgcagct gttgagcgca cctaaccact   1020
ggtcatgccc ccacccctgc tctccgcacc cgcttcctcc cgaccccagg accaggctac   1080
ttctcccctc ctcttgcctc cctcctgccc ctgctgcctc tgatcgtagg aattgaggag   1140
tgtcccgcct gtggctgag aactggacag tggcaggggc tggagatggg tgtgtgtgtg    1200
tgtgtgtgtg tgtgtgtgtg tgtgcgcgcg cgccagtgca agaccgagat tgagggaaag   1260
catgtctgct gggtgtgacc atgtttcctc tcaataaagt tcccctgtga cactcaaaaa   1320
aaaaaaaaa                                                           1329
```

<210> SEQ ID NO 14
<211> LENGTH: 2876
<212> TYPE: DNA
<213> ORGANISM: Homo sapiens
<220> FEATURE:
<223> OTHER INFORMATION: 14-3-3 zeta cDNA (NM_145690) 2876 nt

<400> SEQUENCE: 14

```
gcctgtgagc agcgagatcc agggacagag tctcagcctc gccgctgctg ccgccgccgc     60
cgcccagaga ctgctgagcc cgtccgtccg ccgccaccac ccactccgga cacagaacat    120
ccagtcatgg ataaaaatga gctggttcag aaggccaaac tggccgagca ggctgagcga    180
tatgatgaca tggcagcctg catgaagtct gtaactgagc aaggagctga attatccaat    240
gaggagagga atcttctctc agttgcttat aaaaatgttg taggagcccg taggtcatct    300
tggagggtcg tctcaagtat tgaacaaaag acggaaggtg ctgagaaaaa acagcagatg    360
gctcgagaat acagagagaa aattgagcg gagctaagag atatctgcaa tgatgtactg    420
tctcttttgg aaaagttctt gatcccaat gcttcacaag cagagagcaa agtcttctat    480
ttgaaaatga aggagatta ctaccgttac ttggctgagg ttgccgctgg tgatgacaag     540
aaagggattg tcgatcagtc acaacaagca taccaagaag cttttgaaat cagcaaaaag    600
gaaatgcaac caacacatcc tatcagactg gtctggccc ttaacttctc tgtgttctat     660
tatgagattc tgaactcccc agagaaagcc tgctctcttg caaagacagc ttttgatgaa    720
gccattgctg aacttgatac attaagtgaa gagtcataca aagacagcac gctaataatg    780
caattactga gagacaactt gacattgtgg acatcggata cccaaggaga cgaagctgaa    840
gcaggagaag gagggaaaa ttaaccggcc ttccaacttt tgtctgcctc attctaaaat    900
ttacacagta gaccatttgt catccatgct gtcccacaaa tagtttttg tttacgattt    960 atgacaggtt tatgttactt ctatttgaat ttctatattt cccatgtggt ttttatgttt   1020
aatattaggg gagtagagcc agttaacatt tagggagtta tctgttttca tcttgaggtg   1080
gccaatatgg ggatgtggaa tttttataca agttataagt gtttggcata gtactttgg    1140 tacattgtgg cttcaaaagg gccagtgtaa aactgcttcc atgtctaagc aaagaaaact   1200
gcctacatac tggtttgtcc tggcggggaa taaaagggat cattggttcc agtcacaggt   1260
gtagtaattg tgggtacttt aaggtttgga gcacttacaa ggctgtggta gaatcatacc   1320
ccatggatac cacatattaa accatgtata tctgtggaat actcaatgtg tacacctttg   1380
actacagctg cagaagtgtt cctttagaca agttgtgac ccattttact ctggataagg    1440
gcagaaacgg ttcacattcc attatttgta aagttacctg ctgttagctt tcattatttt   1500
tgctacactc attttatttg tatttaaatg ttttaggcaa cctaagaaca aatgtaaaag   1560
taaagatgca ggaaaaatga attgcttggt attcattact tcatgtatat caagcacagc   1620
```

-continued

```
agtaaaacaa aaacccatgt atttaacttt tttttaggat ttttgctttt gtgattttt    1680 ttttttttt  ttgatacttg cctaacatgc atgtgctgta aaatagtta  acagggaaat    1740 aacttgagat gatggctagc tttgtttaat gtcttatgaa attttcatga acaatccaag    1800
cataattgtt aagaacacgt gtattaaatt catgtaagtg gaataaaagt tttatgaatg    1860
gacttttcaa ctactttctc tacagctttt catgtaaatt agtcttggtt ctgaaacttc    1920
tctaaaggaa attgtacatt ttttgaaatt tattccttat tccctcttgg cagctaatgg    1980
gctcttacca agtttaaaca caaaatttat cataacaaaa atactactaa tataactact    2040
gtttccatgt cccatgatcc cctctcttcc tccccaccct gaaaaaaatg agttcctatt    2100
ttttctggga gaggggggga ttgattagaa aaaaatgtag tgtgttccat ttaaaatttt    2160
ggcatatggc attttctaac ttaggaagcc acaatgttct tggcccatca tgacattggg    2220
tagcattaac tgtaagtttt gtgcttccaa atcacttttt ggttttttaag aatttcttga    2280 tactcttata gcctgccttc aattttgatc ctttattctt tctatttgtc aggtgcacaa    2340
gattaccttc ctgttttagc cttctgtctt gtcaccaacc attcttactt ggtggccatg    2400
tacttggaaa aaggccgcat gatctttctg gctccactca gtgtctaagg caccctgctt    2460
cctttgcttg catcccacag actatttccc tcatcctatt tactgcagca aatctctcct    2520
tagttgatga gactgtgttt atctcccttt aaaacctac  ctatcctgaa tggtctgtca    2580
ttgtctgcct ttaaaatcct tcctctttct tcctcctcta ttctctaaat aatgatgggg    2640
ctaagttata cccaaagctc actttacaaa atatttcctc agtactttgc agaaaacacc    2700
aaacaaaaat gccattttaa aaaaggtgta tttttctttt tagaatgtaa gctcctcaag    2760
agcagggaca atgttttctg tatgttctat tgtgcctagt acactgtaaa tgctcaataa    2820
atattgatga tgggaggcag tgagtcttga tgataagggt gagaaactga aatccc       2876
```

```
<210> SEQ ID NO 15
<211> LENGTH: 31
<212> TYPE: DNA
<213> ORGANISM: Artificial Sequence
<220> FEATURE:
<223> OTHER INFORMATION: Description of Artificial Sequence: Synthetic
      primer used for PCR amplification of the 14-3-3 eta cDNA

<400> SEQUENCE: 15
gcgaattcct gcagcgggcg cggctggccg a                                    31

<210> SEQ ID NO 16
<211> LENGTH: 31
<212> TYPE: DNA
<213> ORGANISM: Artificial Sequence
<220> FEATURE:
<223> OTHER INFORMATION: Description of Artificial Sequence: Synthetic
      primer used for PCR amplification of the 14-3-3 eta cDNA

<400> SEQUENCE: 16
gctcgagcct gaaggatctt cagttgcctt c                                    31
```